US006002778A

United States Patent [19]

Rossetti et al.

[11] Patent Number: 6,002,778

[45] Date of Patent: Dec. 14, 1999

[54] ACTIVE STRUCTURAL CONTROL SYSTEM AND METHOD INCLUDING ACTIVE VIBRATION ABSORBERS (AVAS)

[75] Inventors: Dino J. Rossetti, Chapel Hill; Douglas E. Ivers, Cary; Mark A. Norris, Apex; Michael C. Heath, Cary; Steve C. Southward, Apex, all of N.C.

[73] Assignee: Lord Corporation, Cary, N.C.

[21] Appl. No.: 08/693,742

[22] Filed: Aug. 7, 1996

[51] Int. Cl.[6] .................... A61F 11/06

[52] U.S. Cl. .................... 381/71.4; 381/71.9; 381/71.12

[58] Field of Search .................... 381/71.2, 71.4, 381/71.7, 71.8, 71.9, 71.12; 415/119

[56] References Cited

U.S. PATENT DOCUMENTS

| | | | |
|---|---|---|---|
| 3,487,888 | 1/1970 | Adams et al. | 181/33 |
| 3,490,556 | 1/1970 | Bennett, Jr. et al. | 181/33 |
| 3,566,993 | 3/1971 | Leatherwood et al. | 188/1 |
| 3,836,098 | 9/1974 | Miyashita | 244/17.27 |
| 3,865,508 | 2/1975 | Nagler . | |
| 3,917,246 | 11/1975 | Gartner et al. | 267/136 |
| 4,083,433 | 4/1978 | Geohegan, Jr. et al. | 188/1 B |
| 4,153,815 | 5/1979 | Chaplin et al. | 381/71.9 |
| 4,202,237 | 5/1980 | Hakansson . | |
| 4,365,770 | 12/1982 | Mard et al. | 244/17.11 |
| 4,689,821 | 8/1987 | Salikuddin et al. | 381/71.9 |
| 4,715,559 | 12/1987 | Fuller | 244/1 N |
| 4,878,188 | 10/1989 | Ziegler, Jr. | 364/724.01 |
| 5,010,573 | 4/1991 | Hill | 381/71 |
| 5,065,959 | 11/1991 | Bhatia et al. . | |
| 5,146,505 | 9/1992 | Pfaff et al. | 381/71 |
| 5,174,552 | 12/1992 | Hodgson et al. . | |
| 5,209,326 | 5/1993 | Harper | 188/378 |
| 5,219,143 | 6/1993 | Staple et al. | 248/550 |
| 5,233,540 | 8/1993 | Andersson et al. | 364/508 |
| 5,245,552 | 9/1993 | Andersson et al. | 364/508 |
| 5,251,863 | 10/1993 | Gossman et al. | 248/550 |
| 5,310,137 | 5/1994 | Yoerkie, Jr. et al. | 244/17.27 |

(List continued on next page.)

FOREIGN PATENT DOCUMENTS

| | | | |
|---|---|---|---|
| 2 122 052 | of 0000 | United Kingdom | F16F 15/00 |
| WO 95/34769 | 12/1995 | WIPO . | |
| WO 96/12121 | 4/1996 | WIPO . | |

OTHER PUBLICATIONS

M.R. Jolly, et al. "Passive Tuned Vibration Absorbers for Sound Radiation Reduction from Vibrating Panels" *Journal of Sound and Vibration* (1996) pp. 577–583.

(List continued on next page.)

*Primary Examiner*—Vivian Chang
*Attorney, Agent, or Firm*—Randall S. Wayland

[57] ABSTRACT

An Active Structural Control (ASC) system (10) and method which includes a plurality of Active Vibration Absorbers (AVAs) (40) attached to a yoke (32) included within a pylon structure (28) preferably comprising a spar (38) and a yoke (32) which is located intermediate between an aircraft fuselage (20) and an aircraft engine (18) for controlling acoustic noise and/or vibration generated within the aircraft's cabin (44) due to unbalances in the aircraft engine (18). The ASC system (10) includes a plurality of error sensors (42) for providing error signals, and at least one reference sensor (49 or 50) for providing reference signals indicative of the N1 and/or N2 engine rotations and/or vibrations, and a preferably digital electronic controller (46) for processing the error and reference signal information to provide output signals to drive the plurality of AVAs (40) attached to the yoke (32). The AVAs (40) preferably act in a radial, tangential, or fore and aft directions and may be preferably located at the terminal end and/or at the base portion of the yoke (32). Further, the AVAs (40) may be Single Degree Of Freedom (SDOF) or Multiple Degree Of Freedom (MDOF) and may be tuned to have a passive resonance which substantially coincides with the N1 and/or N2 engine rotation and/or vibrations. In another aspect, reference signal processing is described which includes a modulo counter, a lookup table, and a digital IO.

12 Claims, 16 Drawing Sheets

U.S. PATENT DOCUMENTS

| | | | |
|---|---|---|---|
| 5,332,061 | 7/1994 | Majeed et al. | 180/312 |
| 5,348,124 | 9/1994 | Harper | 188/378 |
| 5,386,689 | 2/1995 | Bozich et al. . | |
| 5,423,658 | 6/1995 | Pla et al. . | |
| 5,515,444 | 5/1996 | Burdisso et al. . | |
| 5,530,764 | 6/1996 | Uchida et al. | 381/71.4 |
| 5,551,650 | 9/1996 | Southward et al. . | |
| 5,687,948 | 11/1997 | Whiteford et al. . | |

OTHER PUBLICATIONS

J. Q. Sun, et al. "Passive, Adaptive and Active Tuned Vibration Absorbers—A Survey" *Transactions of the ASME*; Jun. 1995; vol. 117; pp. 234–242.

J. Van Dyke, Jr.et al., "Cabin Noise Reduction in the DC–9", Jun. 12–14, 1967, No. 67–401.

Andreas II, von Flotow et al., Adaptive Tuned Vibration Absorbers: Tuning Laws, Tracking Agility, Sizing and Physical Implementation, Noise–Con 94, May 1–4, 1994.

J.L. Potter et al., "Elastomers+Fluids+Electronics=Improved Comfort and Reliability for Aircraft", Twenty–First European Rotorcraft Forum, Aug. 30–Sep. 1, 1995, Paper No. III.5.

J.Q. Sun et al., "Theoretical and Experimental Studies of Distributed Piezoelectric Actuators for Interior Noise Control", Lord Corporation, Thomas Lord Research Center, Feb. 1994.

Rossetti et al., "A Comparison of Actuation and Sensing Techniques for Aircraft Cabin Noise. Control", Dec. 12, 1995, Noise Control Eng. J 44(1), 1996 Jan.–Feb.

Jolly et al., "A Demonstration of Active Control for Helicopter Cabin Noise Reduction", Oct. 1994.

Steve C. Southward, "Centralized vs. Decentralized: Optimal Steady–State Tonal Control for Multi–Channel Systems", Thomas Lord Research Center, Nov. 1992.

Steve C. Southward, "Filter Length Sizing for the Filtered–X LMS Algorithm in Large Mimo Tonal Noise Cancellatiuon Systems", DE–vol. 75, Active Control of Vibration and Noise, ASME Jan. 1994.

Steve C. Southward, "Feedforward Control Using the Higher–Harmonic, Time–Averaged Gradient Descent Algorithm", J. Acoust. Soc. Am. 97(5), Pt. 1, May 1995.

D.J. Rossetti, "Passive, Active, and Hybrid Solutions for Aircraft Interior Noise Problems", Thomas Lord Research Center, Nov. 1995.

Ahmadian et al., "Performance Analysis of Active Mounts fot Structural Vibration Reduction", Lord Corporation, Apr. 1993.

Ivers et al., "Active Mounting System Flight Test Results", Inter–noise, Jul. 10–12, 1995.

Simpson et al., "Full–Scale Demonstration Tests of Cabin Noise Reduction Using Active Vibratuon Control", AIAA 12th Aeroacoustics Conference, Apr. 10–12, 1989, Douglas Paper 8152, AIAA–89–1074.

Sommerfeldt, "Adaptive Control of a Two–Stage Vibration Mount:", FA13–10:45, Jan. 1988.

Lord Mechanical Products, "Lord YVX™ Systems for Axtive Noise and Vibration Control", Jan. 1994, Lord Corporation, PB 6012.

Lord Corporation Brochure, Lord Corporation Reports Major Advanxement in Noise and Vibration Control Technology, Jan. 1994.

Lord Mechanical Products Brochure, "Active Isolation Systems and Active Structural Control", , Jan. 1993, PB6009.

Larry J. Eriksson, Digisonix, "A Primer on the Digisonix Approach to Active Sound and Vibration Control", Jan. 1994.

Lancaster, CMOS Codebook, Jan. 1979, pp. 366–367, 1979.

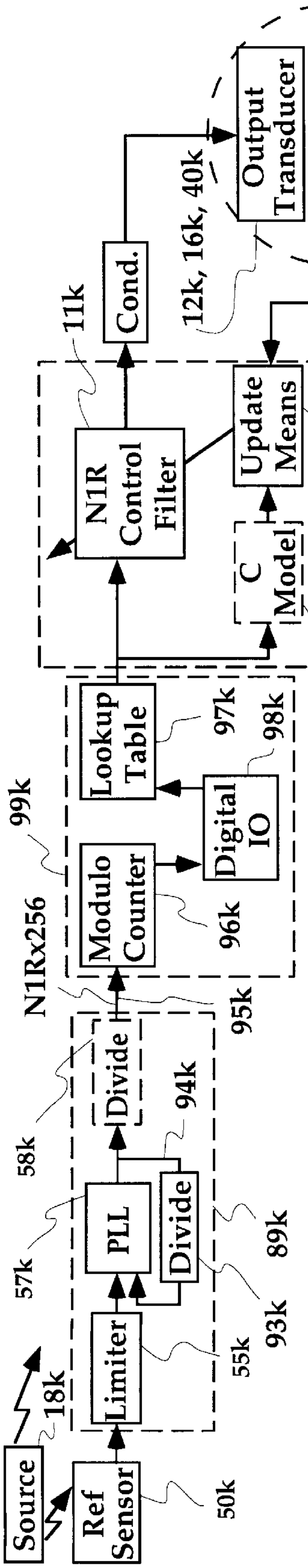
Fig. 7a
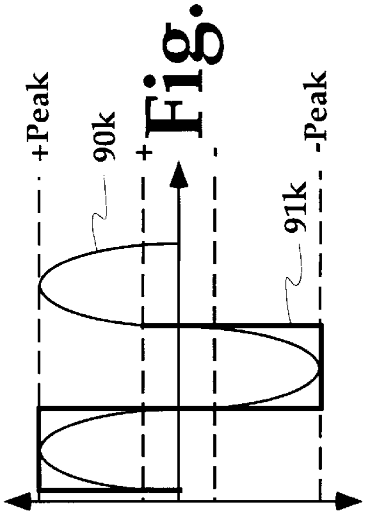
Fig. 7b
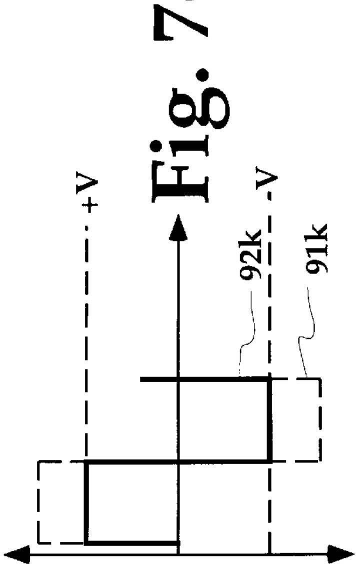
Fig. 7c
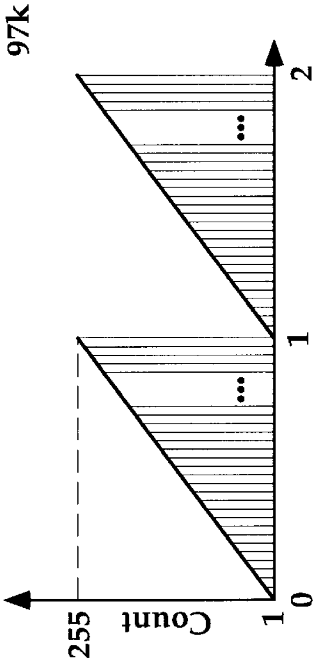
Fig. 7d
97k
| Count | Input Signal |
|---|---|
| 0 | 0.0000 |
| 1 | 0.0245 |
| 2 | 0.0491 |
| • | • |
| 64 | 1.0000 |
| • | • |
| 128 | 0.0000 |
| • | • |
| 255 | -0.0245 |
Fig. 7e

ACTIVE STRUCTURAL CONTROL SYSTEM AND METHOD INCLUDING ACTIVE VIBRATION ABSORBERS (AVAS)

FIELD OF THE INVENTION

This invention relates to the area of systems and methods for controlling acoustic noise and vibration within an aircraft's cabin. Specifically, it relates to actively-controlled devices and methods for controlling noise and vibration via Active Structural Control (ASC) methods.

BACKGROUND OF THE INVENTION

Irritating and annoying acoustic noise and dynamic vibration can be created within an aircraft's cabin due to rotational unbalances and the like of the aircraft's engine(s). For example, on fuselage-mounted aircraft engines, the rotational unbalance(s) cause vibration to be transmitted into the yoke structure, through the intermediate spar structure, and into the aircraft's fuselage. If the vibration of the fuselage is well coupled to the acoustic space within the aircraft's cabin, then annoying, predominantly tonal sound (generally characterized as a low frequency irritating drone) can be generated therewithin. In particular, this drone generally corresponds with the most dominant engine tones, for example, the tones created via the N1 and N2 engine rotations. In aircraft with aft-fuselage-mounted engines, such as the McDonnell Douglas DC-9 aircraft, any rotational unbalance of the engines may result in unwanted and annoying low frequency noise being generated within the aircraft's cabin, and specifically in the aft portion thereof. In general, passengers in the aft portion of the cabin experience this low-frequency tonal noise (drone) related to the N1 and N2 tones of the engine. The N1 and N2 tones are generated by rotational unbalances of the turbine (fan) and compressor stages (compressor) of attached multistage jet engines. Elimination of the N1 and N2 tones can dramatically reduce the discomfort experienced by the passengers, particularly in the aft-most portion of the aircraft's cabin.

Within the prior art, various means have been employed to counter aircraft cabin acoustic noise. These include passive blankets, passive Tuned Vibration Absorbers (TVAs), adaptive TVAs, Active Noise Control (ANC), Active Structural Control (ASC), and Active Isolation Control (AIC). Passive blankets are generally effective in attenuating higher-frequency noise, but are generally ineffective at attenuating low-frequency noise of the type described herein, i.e., low-frequency drone. Furthermore, passive blankets must be massive to reduce low-frequency noise transmission into the cabin. Passive Tuned Vibration Absorbers (TVAs) may be effective at attenuating low-frequency noise, but are generally limited in range and effectiveness. Passive TVAs include a suspended mass which is tuned (along with a stiffness) such that the device exhibits a resonant natural frequency (fn) which generally cancels or absorbs vibration of the vibrating member at the point of attachment thereto. The afore-mentioned disadvantage of passive TVAs is that they are only effective at a particular frequency (fn) or within a very narrow frequency range thereabouts. Therefore, TVAs may be ineffective if the engine frequency is changed and the TVA is not operating at its resonant frequency. Furthermore, passive devices may be unable to generate the proper magnitude and phasing of forces needed for effective vibration suppression and/or control. Passive TVAs are generally attached to the interior stiffening rings or stringers of the fuselage or to the yoke. U.S. Pat. No. 3,490,556 to Bennett, Jr. et al. entitled:

"Aircraft Noise Reduction System With Tuned Vibration Absorbers" describes a passive vibration dampening device for use on the pylon of an aircraft for absorbing vibration at the N1 and N2 rotational frequencies.

When a wider range of vibration cancellation is required, various adaptive TVAs may be employed. For example, U.S. Pat. No. 3,487,888 to Adams et al. entitled "Cabin Engine Sound Suppresser" teaches an adaptive TVA where the resonant frequency (fn) can be adaptively adjusted by changing the length of the beam or the rigidity of a resilient cushioning material. Although, the range of vibration attenuation may be increased with adaptive TVAs, they still may be ineffective for certain applications, in that their range of adjustment may not be large enough or they may not be able to generate enough dynamic forces to adequately reduce acoustic noise or vibration experienced within the aircraft's cabin.

In some applications where a higher level of noise attenuation is desired, Active Isolation Control (AIC) systems provide another means for controlling noise within an aircraft's cabin. In Prior Art FIG. 1, an aircraft with multiple aft-fuselage-mounted turbofan engines is shown. AIC systems include active mountings, such as 12*a*, 12*b*, 12*c*, and 12*d*, which include an actively driven element contained therein, to provide the active control forces for isolating vibration and preventing its transmission from the engines 18L and 18R into the pylon structures 28L and 28R. The resultant effect is preferably a reduction of annoying interior acoustic noise in the aircraft's cabin 44. Known AIC systems include the feedforward type, in that reference signals, such as from reference accelerometers 49L and 49R, are used to provide a reference signal indicative of the N1 and N2 vibrations of engines, 18L and 18R. Error sensors, such as a plurality of microphones 42, provide error signals indicative of the residual noise at various locations in the aircraft cabin 44. Specifically, in known AIC systems, active mountings, such as 12*a–d* are attached between an aircraft yoke 32L and 32R and the aircraft's engine 18L and 18R. The reference signals and error microphones 42 are processed by a digital controller 46 to generate drive signals of the appropriate phase and magnitude (anti-vibration) to reduce vibration transmission from the engine to the yoke, and resultantly controlling and/or reducing the interior acoustic noise.

Copending U.S. patent application Ser. No. 08/260,945 entitled "Active Mounts For Aircraft Engines" describes several AIC systems. Furthermore, commonly assigned U.S. Pat. No. 5,174,552 to Hodgson et al. entitled "Fluid Mount With Active Vibration Control" describes the details of one type of active fluid mounting. It should be understood, that in some applications, there may be insufficient space envelope to incorporate the active element within the active mounting. Furthermore, there may be alternate vibration paths into the structure or the appropriate actuation directions required for vibration attenuation may be difficult to accomplish within the environment of an active mounting. Furthermore, modification to the mounting system, to incorporate active elements may reduce the amount of load bearing surface, possibly reducing the drift-life expectancy of the mounting system.

Active Noise Control (ANC) systems are also well known. As described with reference to Prior Art FIG. 2, ANC systems may be used on turboprop aircraft or the like, and include a plurality of acoustic output transducers, such as loudspeakers 16*a*, 16*b*, 16*c*, and 16*d*, strategically located within the aircraft's cabin 44 and attached to the aircraft's trim. These loudspeakers are driven responsive to input signals from input sensors and error signals from error sensors 42 disbursed within the aircraft's cabin 44. Input signals may be derived from engine tachometers, accelerometers, or the like, which are placed on the engines 18L and 18R, or reference sensors 14L and 14R located on the fuselage in the area of the aerodynamic propeller wash generated by the propellers 17L and 17R driven by engines 18L and 18R mounted on wings 15L and 15R. The output signals to the loudspeakers 16*a*–16*d*, in ANC systems are generally adaptively controlled via a digital controller 46 according to a known feedforward type adaptive control algorithm, such as the Filtered-x Least Mean Square (LMS) algorithm, or the like. Copending U.S. patent application Ser. No. 08/553,227 to Billoud entitled "Active Noise Control System For Closed Spaces Such As Aircraft Cabins" describes one such ANC system. ANC systems have the disadvantage that they do not generally address any mechanical vibration problems and may be difficult to retrofit to existing aircraft. Furthermore, as the frequency of noise increases, large numbers of error sensors and speakers are required to achieve sufficient global noise attenuation.

Certain ASC systems, known in the prior art, may solve this problem of needing a large number of error sensors by attacking the vibrational modes of the aircraft's fuselage directly. For example, by attaching "a vibrating device such as an actuator or a shaker which is directly connected to the interior surface of the fuselage in order to introduce a vibration directly into the fuselage surface", as described in U.S. Pat. No. 4,715,559 to Fuller, global attenuation can be achieved with a minimal number of error sensors. However, the modifications necessary to retrofit AVAs in this manner may be prohibitive, as the interior trim may have to be removed and structural modifications made have to be made to the stringers or stiffening-ring frames. Furthermore, for control of N2 tones, an exceedingly large number of AVAs may be needed. Therefore, prior art ASC systems are necessarily difficult to retrofit and may require the use of many shaker/actuators to effectuate control of higher-order tones. U.S. Pat. No. 5,310,137 to Yoerkie, Jr. et al. describes the use of AVAs to cancel high-frequency vibrations of a helicopter transmission. Notably, Yoerkie, Jr. et al. is a feedback-type system.

Further descriptions of AVAs and active mounts can be found in Copending U.S. application Ser. No. 08/322,123 entitled "Active Tuned Vibration Absorber" and copending PCT application PCT/US95/13610 entitled "Active Systems and Devices Including Active Vibration Absorbers (AVAs)."

Therefore, there is a recognized need for an ASC system which provides active attenuation to effectively minimize vibration within the structure attached between the engine and the fuselage of an aircraft with the result of reducing annoying acoustic noise and mechanical vibration within the aircraft's cabin throughout its entire frequency range, and without the need for major modification of the fuselage or the aircraft engine mountings, thus allowing ease of retrofit of the system.

SUMMARY OF THE INVENTION

Therefore, in light of the advantages and drawbacks of the prior art, the present invention is an Active Structural Control (ASC) system of the type useful for control of noise and/or vibration caused by aircraft engines, e.g., aft-fuselage-mounted turbofan engines. In the ASC system, vibration is controlled within a yoke structure of the aircraft which interconnects between the spar and aircraft engine. The yoke and spar comprise, in general, a pylon structure which interconnects between at least one aircraft engine and the aircraft's fuselage. The ASC system comprises a plurality of error sensors for providing a plurality of error signals representative of the residual noise or vibration, and in the case of the aft-fuselage-mounted engine, are preferably located at an aft-most portion of said aircraft cabin. At least one reference sensor associated with said at least one engine provides at least one reference signal selected from the group consisting of a first reference signal indicative of an N1 engine rotation and a second reference signal indicative of an N2 engine rotation. A plurality of Active Vibration Absorbers (AVAs) are attached to said yoke with various preferable orientations, and with preferable tuning to increase efficiency. A digital electronic controller is used for processing said at least one reference signal and said plurality of error signals according to a feedforward-adaptive algorithm, such as filtered-x Least Mean Square (LMS) to update weights within a plurality of control filters. The output from the plurality of control filters provide a plurality of output signals to said plurality of AVAs. The ensuing effect is control of vibration within said yoke, which resultantly controls acoustic noise and/or vibration within said aircraft's cabin.

It is an advantage that the present invention ASC system can be easily retrofitted to existing turbofan aircraft, in the field, without extensive modification thereto.

It is an advantage that the present invention ASC system can control vibration of the yoke over a wide frequency range, thereby controlling unwanted and annoying acoustic noise within the aircraft's cabin over a wide frequency range.

It is an advantage that the present invention ASC system can control acoustic noise within the aircraft's cabin throughout the engine's operational range.

It is an advantage that the present invention ASC system can generate larger dynamic forces than the prior art passive TVA systems.

It is an advantage that the present invention ASC system can adapt phase.

It is an advantage that the present invention ASC system can control both annoying N1 and N2 tones within the aft portion of the aircraft cabin.

It is an advantage that the present invention ASC system can control the annoying acoustical beat between the engines.

It is an advantage that the present invention ASC system may minimize potentially metal fatigue producing vibration.

The abovementioned and further features, advantages, and characteristics of the present invention will become apparent from the accompanying descriptions of the preferred and other embodiments and attached drawings.

BRIEF DESCRIPTION OF THE DRAWINGS

The accompanying drawings which form a part of the specification, illustrate several key embodiments of the present invention. The drawings and description together, serve to fully explain the invention. In the drawings.

FIG. 7*a* is a schematic block diagram of a ANVC system illustrating one implementation for deriving the input signal (s), FIG. 7*b* and FIG. 7*c* illustrate the reference signal(s) at various points during the conditioning process, FIG. 7*d* illustrates the count versus the cycle, and FIG. 7*e* illustrates a input signal lookup table.

DETAILED DESCRIPTION OF THE INVENTION

Figure 1:
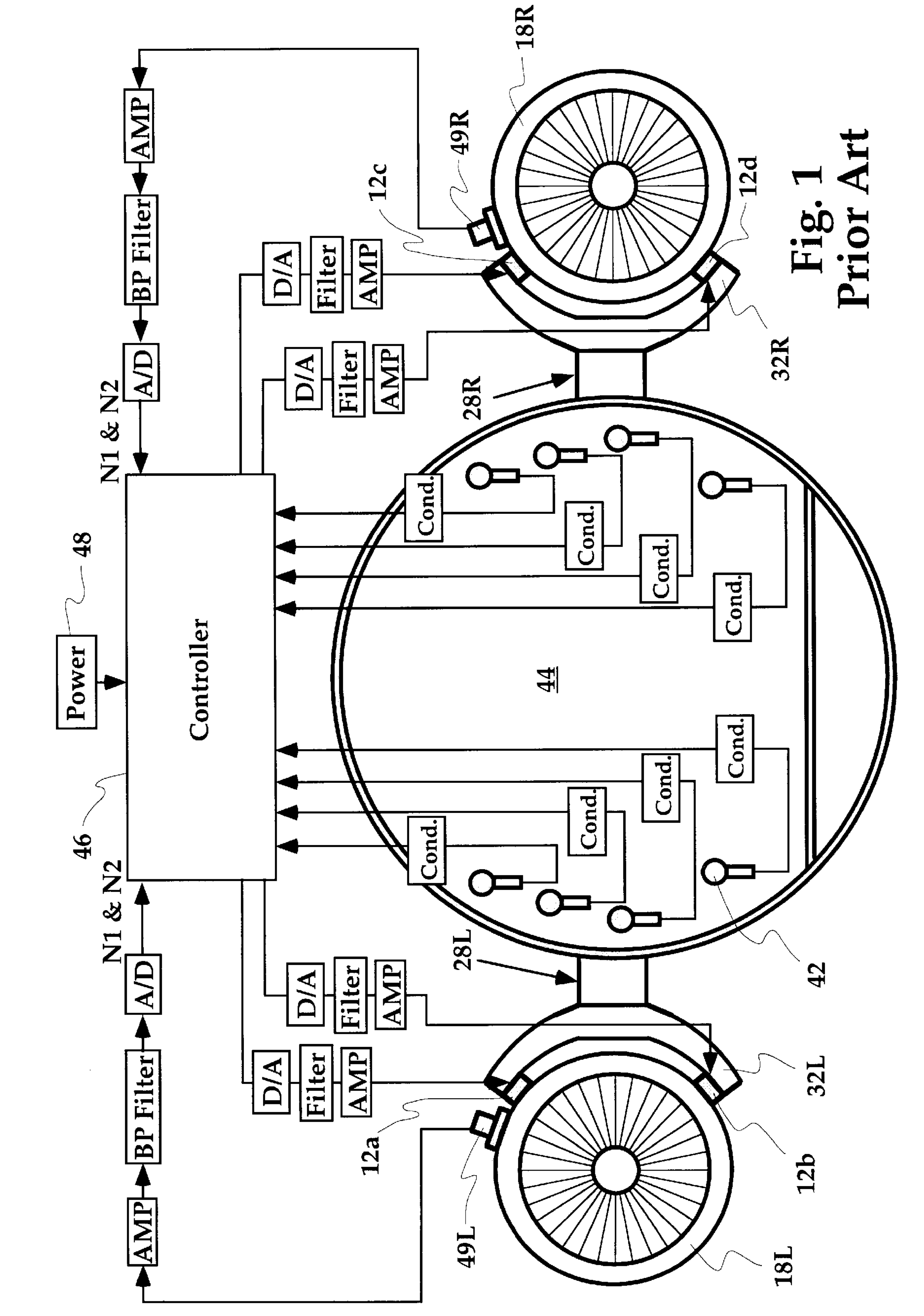
Fig. 1 Prior Art
FIG. 1 is a schematic forward-looking view of a prior art Active Isolation Control (AIC) system including active mountings attached between the engines and yokes.
Figure 2:
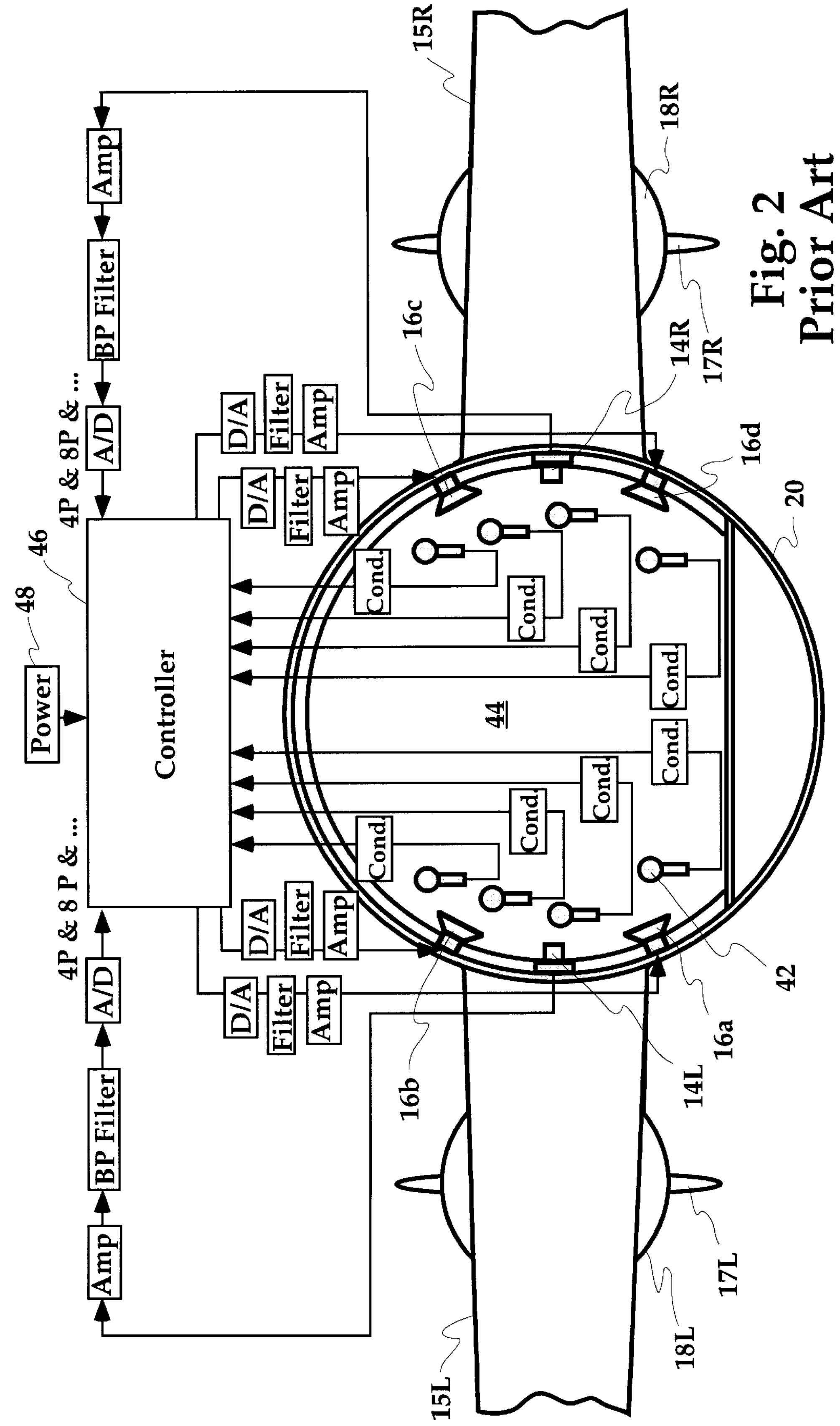
Fig. 2 Prior Art
FIG. 2 is a schematic forward-looking view of a prior art Active Noise Control (ANC) system including loudspeakers located within the cabin for producing
Figure 3A:
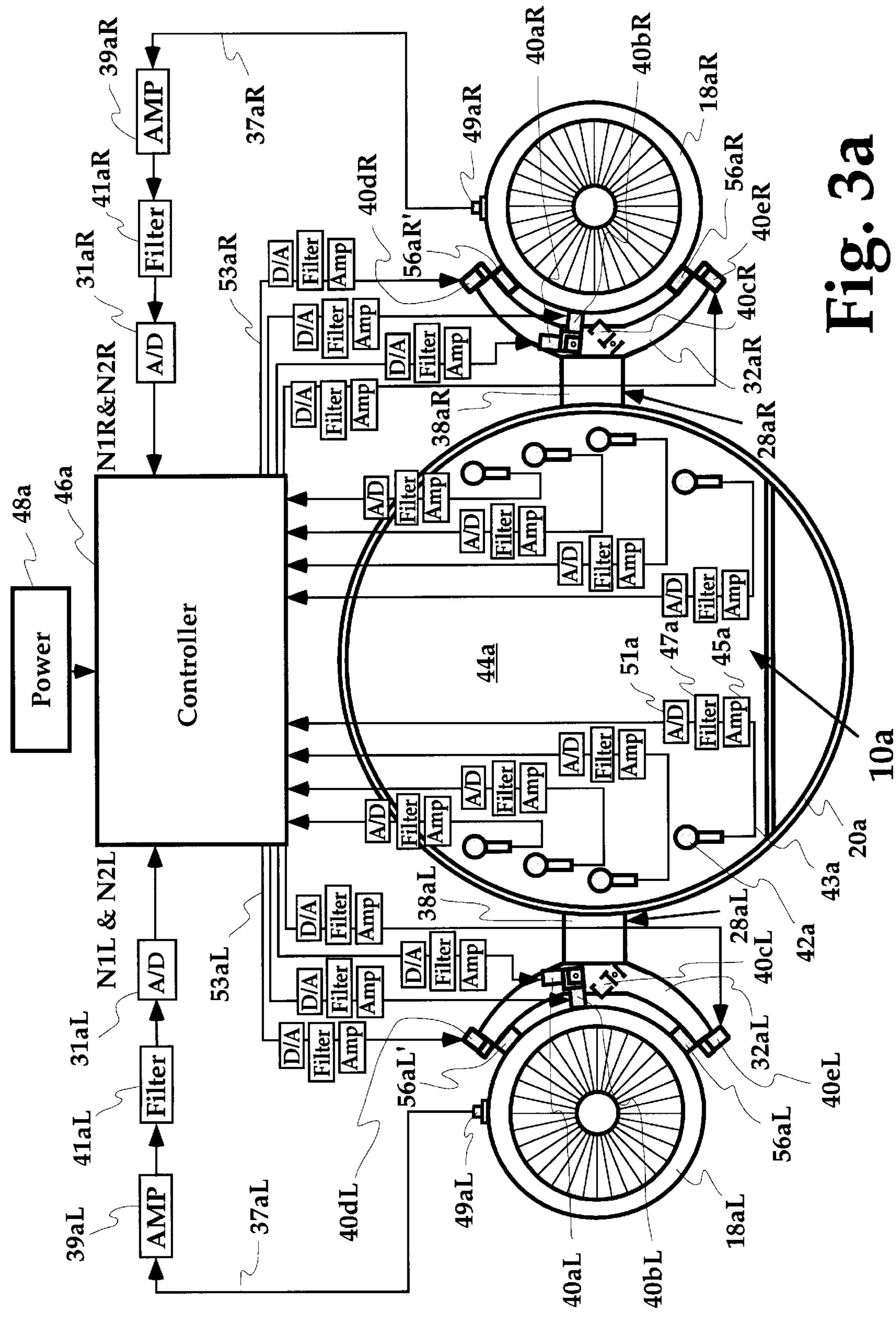
FIG. 3*a* is a schematic forward-looking view of a first present invention ASC system including multiple AVAs attached to the yokes of an aircraft wherein reference signals are derived from accelerometer reference sensors.

Referring now to the Drawings where like numerals denote like elements, in FIG. 3*a*, shown generally at 10*a*, is a first embodiment of the present invention Active Structural Control (ASC) system for controlling annoying acoustic noise and/or vibration generated within an aircraft's cabin 44*a*. This invention has particular applicability for aft-fuselage-mountedturbofan aircraft, such as the DC-9aircraft including, by way of example, aft-fuselage-mounted Pratt & Whitney JT8D engines. The noise and/or vibration in the cabin 44*a* result from vibration generated by a rotational unbalance or the like of at least one engine, and in this example, two aft-fuselage-mounted turbofan jet engines, 18*a*L and 18*a*R. The dynamic mechanical vibration is transmitted into the pylon structures, 28*a*L and 28*a*R, which are attached on either side of the fuselage 20*a*. Each pylon structure 28*a*L and 28*a*R includes crescent-shaped yokes, 32*a*L and 32*a*R, and generally radially extending spars, 38*a*L and 38*a*R. Transmitted vibration from engines 18*a*L and 18*a*R cause vibration of the fuselage 20*a*.

Vibration of the fuselage and various passive means for controlling cabin noise therein are further described in AIAA paper No. 67-401 entitled "Cabin Noise Reduction in the DC-9 Aircraft" by J. VanDyke, Jr., J. Schendel, C. Gunderson, and M. Ballard. The vibration of the fuselage 20*a* generates irritating acoustic noise and/or vibration within said aircraft's cabin 44*a* with dominant tones that generally emerge at the N1 and N2 engine rotation frequencies. It was discovered by the inventors, that by the novel active control of the residual vibration within the yoke, 32*a*L and 32*a*R, the tonal noise generated by both the N1 low-speed rotor vibration and N2 high-speed rotor vibration of the engines 18*a*L and 18*a*R may both be reduced over their operating range. Higher-order tones (such as those coincident with 2N1) may also be controlled. In short, the invention herein described is an apparatus for actively controlling the vibration of the yokes 32*a*L and 32*a*R with the resultant effect of controlling unwanted noise and/or vibration occurring within the cabin 44*a*.

In particular, the noise reduction tracks changes in the engine(s) speed, thus, allowing for noise and vibration control/reductions over the wide range of frequencies associated with N1 and N2. Specifically, the noise associated with N1 and N2 can be as high as 110 dB, or more at N1 and N2 without active control. The present invention generally reduces the N1 and N2 tones down to the background noise (by as much as 20 dB or more, See FIG. 3*h*).

The ASC system 10*a* is comprised of a plurality of error sensors 42*a*, such as microphones shown, strategically arranged and equally spaced about the aircraft cabin 44*a*, and in particular, for the aft-fuselage-mounted engine case, the error sensors 42*a* are preferably only located in the aft portion (preferably the aft ½ portion—between the aft galley and the rear wing spar) of the cabin 44*a*, for providing a plurality of error signals, via plurality of error cables 43*a* attached thereto, directly to the digital electronic controller 46*a*. It was discovered by the inventors that placing the plurality of error sensors 42*a* only in the aft portion in the aft-fuselage-mounted engine case, it was possible to effectuate a reduction there, but also elsewhere in the cabin 44*a*. In this case, the error signals are representative of the residual acoustic noise within the aft portion of the aircraft cabin 44*a* at the location of each of the plurality of error sensors 42*a*. The error path includes amps 45*a*, filters 47*a*, and Analog-to-Digital (A/D) converters 51*a*. It should be understood that these elements may be housed within the box/housing containing the controller, and are shown separately for clarity. The amps 45*a* amplify the error signal to appropriate levels and may include further conditioning. The filters 47*a*, such as a low pass filter, high pass filter, band pass filter, or combinations thereof, filter out signal portions outside the frequency range of control to provide relatively noise-free error signals (containing only frequency information within the control frequency range). The A/D converter 51*a* converts the analog signal into a useable digital form to be processed in digital form by the digital electronic controller 46*a*. The error signals may be sampled at either a constant or variable sampling rate.

By way of example, eight error sensors 42*a* are shown in this cross-section of the fuselage 20*a*. The actual number n of error sensors 42*a*, preferably located in the aft-most portion of fuselage 20*a*, will vary by application. Generally, the number n of error sensors 42*a* will be selected based upon the number m of AVAs present in the system. It is generally understood that the number of error sensors 42*a* should be equal to, or greater than, the number of AVAs. By way of example, and not by limitation, the preferred ASC system includes about 16 error microphones in the aft ½ portion of the aircraft cabin and about 8–12 AVAs (4–6 per engine). The error sensors 42*a* are preferably placed in a plane adjacent to the passengers' head height or thereabouts on either side of the aircraft cabin. Optionally, accelerometers may be used as the error sensors, as will be explained with reference to FIG. 4*b*.

In more detail, the ASC system 10*a* includes at least one reference sensor for providing a reference signal representative of the frequency (and possibly the magnitude) of the N1 and N2 engine vibrations/rotations for each engine 18*a*L and 18*a*R. For example, in this embodiment, two reference accelerometers, 49*a*L and 49*a*R, are provided, one on each engine 18*a*L and 18*a*R, for deriving a first reference signal indicative of an N1 engine vibration and a second reference signal indicative of an N2 engine vibration, for each engine 18*a*L and 18*a*R. Although, shown with one sensor 49*a*L and 49*a*R providing both N1 and N2 information for each engine 18*a*L and 18*a*R, it should be understood that separate sensors may provide the signal indicative of N1 and N2 vibration for each engine, 18*a*L and 18*a*R.

In this embodiment, the accelerometers 49*a*L and 49*a*R would preferably attach to the engine casings at an appropriate point such that each sensor 49*a*L and 49*a*R picks up and transmits the N1 and N2 vibrations for each respective engine 18*a*L and 18*a*R. The reference signals are provided via reference cables 37*a*L and 37*a*R, and in this embodiment, each signal includes vibrational contributions from N1 with superimposed N2 vibrations included thereon. The signals are amplified within input amps 39*a*L and 39*a*R to the appropriate voltage level, filtered by analog input filters 41*a*L and 41*a*R to filter out unwanted frequency information and prevent aliasing, and then input directly into input A/D converters 31*a*L and 31*a*R. The A/D converters preferably sample the analog signal at a constant sample rate of at least about 4 times the N2 frequency or approximately 1000 hz and, thereby, provide digital reference signals indicative of the N1 vibration and the N2 vibration to the controller 46*a*. Optionally, variable rate reference signal sampling could be employed. It should be understood that the input sampling and control filter update process are preferably asynchronous, in that they are not synchronized with the input signal and take place independent thereof. However, synchronous sampling could also be employed as well as a synchronous control method. The input signals, once they are band separated and further conditioned to derive the N1 and N2 digital signals, are then processed digitally (convoluted) with control filters (preferably transversal FIR filters) and summed to generate an output signal for each AVA. Transversal filters are described with reference to FIG. 3*e* and FIG. 3*f*.

Figure 4A:
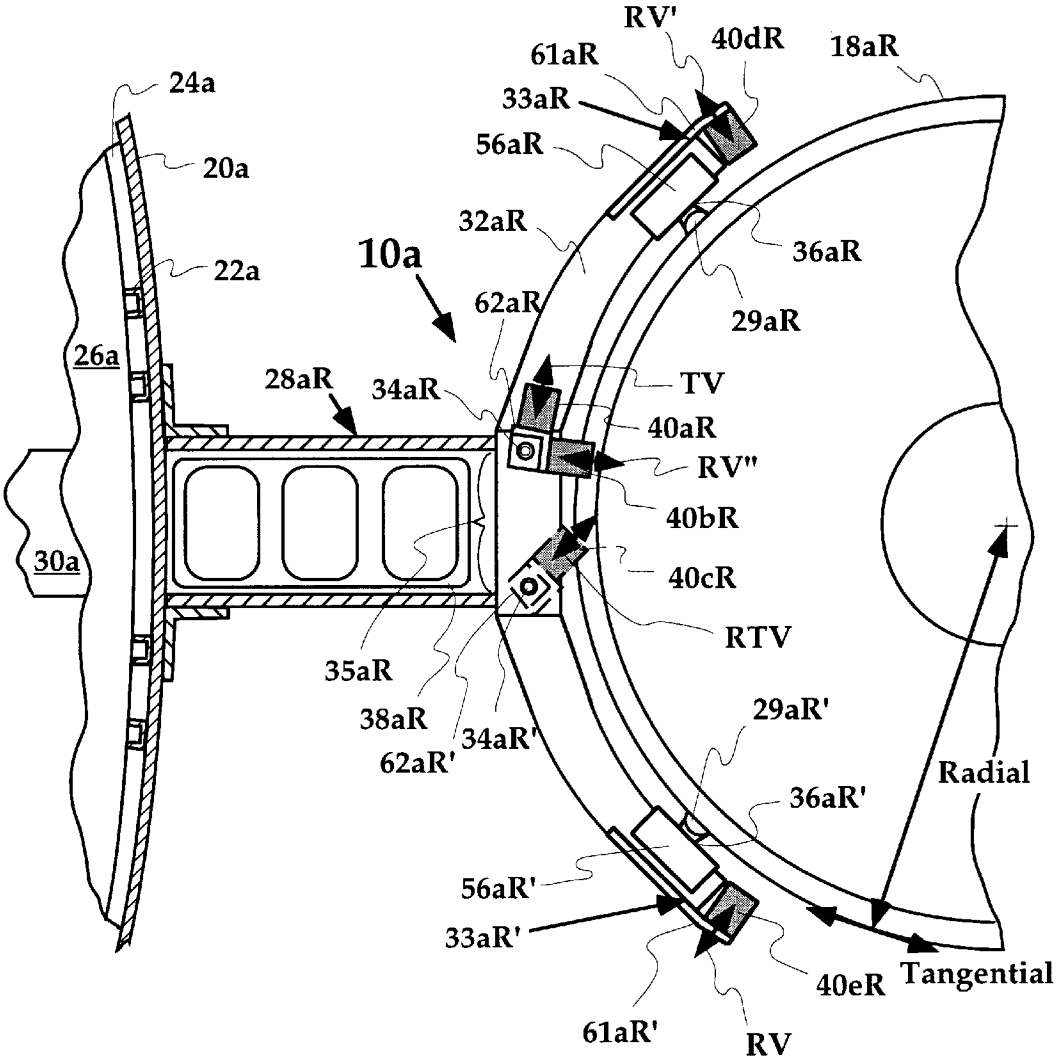
FIG. 4*a* is a detailed partial forward-looking schematic view of the first embodiment of the present invention ASC system illustrating AVA locations/directions on the right yoke.
Figure 5A:
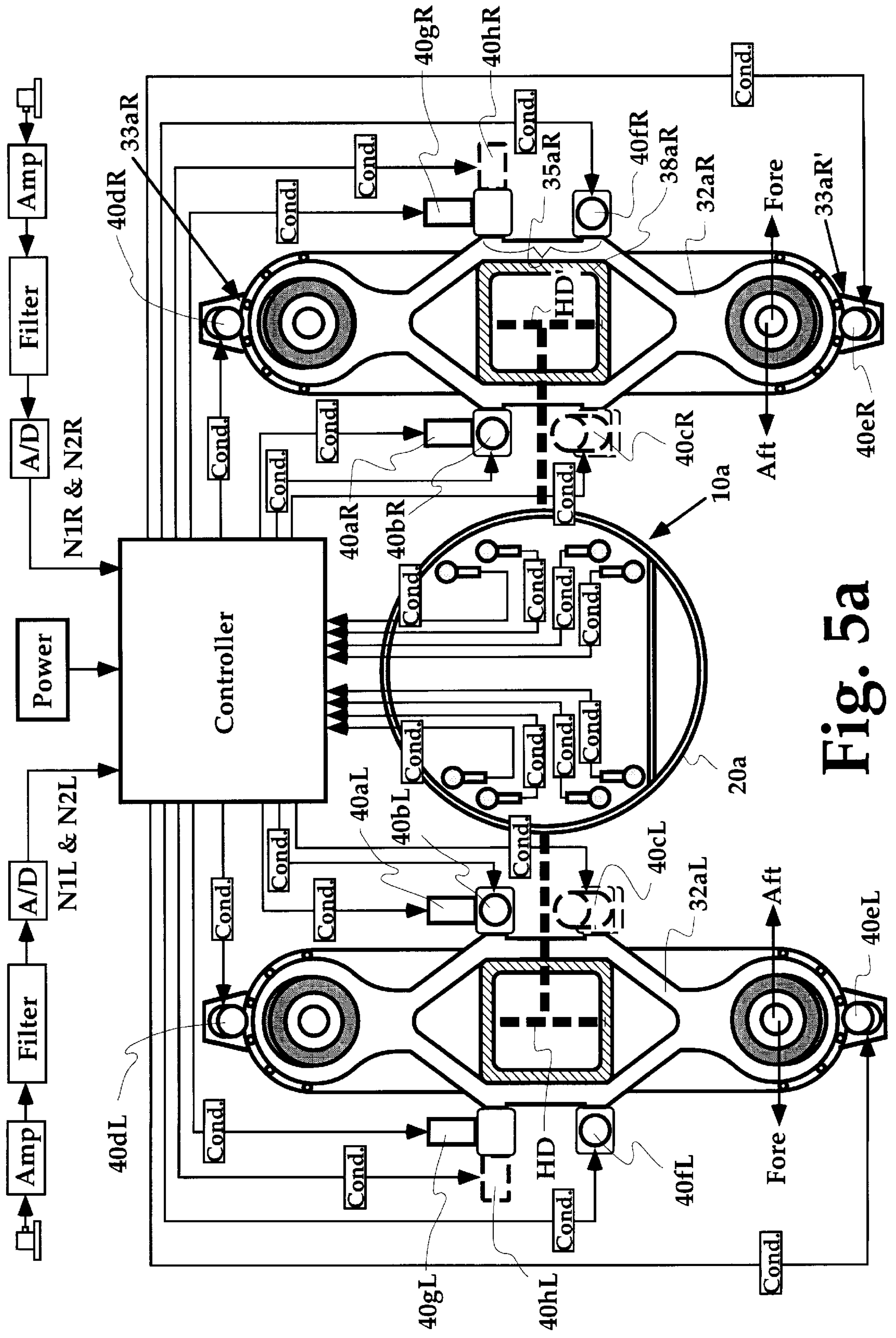
FIG. 5*a* is a schematic diagram of the first embodiment described with reference to FIG. 3*a* including reference accelerometer sensors and illustrating the preferred locations/directions of the plurality of AVAs on the yokes.

Output signals in output cables such as 53*a*L and 53*a*R are provided to drive the plurality of Active Vibration Absorbers (AVAs) (FIGS. 3*a*, 4*a* and 5*a*). The AVAs are directly attached by way of brackets, e.g. 61*a*R, 61*a*R', 62*a*R, 62*a*R' (FIG. 4*a*) to the right and left yokes, 32*a*L and 32*a*R. The number of transversal filters required, in the fully-coupled case, is generally equal to the number of tones being controlled, in this case both N1 and N2 tones are preferably controlled, times the number of engines, in this example two jet engines, 18*a*L and 18*a*R, and finally times the number of AVAs 42*a*L–42*h*L, 42*a*R–42*h*R (in this case, preferably 6 AVAs per engine), or 2×2×12=48 control filters. It should be understood that the number of control filters required is preferably reduced through reference sensor/signal partitioning and/or through error sensor partitioning to be described later.

The left and right yokes, 32*a*L and 32*a*R, attach directly to the left and right spars, 38*a*L and 38*a*R, at the spars' terminal ends, whereas the other end of the spars, 38*a*L and 38*a*R, attaches directly to the fuselage 20*a*. The left and right yokes, 32*a*L and 32*a*R, and left and right spars, 38*a*L and 38*a*R, make up and comprise the left and right pylon structures, 28*a*L and 28*a*R. What are referred to herein as the pylon structures, 28*a*L and 28*a*R, are located intermediate and between the at least one engine, for example 18*a*L and the aircraft's fuselage 20*a*.

A preferably digital electronic controller 46*a* processes said first reference signal(s) and said second reference signal(s) information and said plurality of error signals in an adaptive feedforward fashion and provides a plurality of output signals to said plurality of active vibration absorbers e.g. 40*a*L–40*h*L, 40*a*R–40*h*R (FIG. 5*a*) to directly effectuate control of vibration within said yokes, 32*a*L and 32*a*R, and resultantly globally control acoustic noise generation and mechanical vibration emerging within said aircraft cabin 44*a*, and specifically within the aft portion of the aircraft cabin 44*a*. N1L, N2L, N1R and N2R signals indicative of the vibration of engines 18*a*L and 18*a*R provide reference signals to the control process such that the acoustic noise coincident with the N1 and N2 tones of each engine 18*a*L and 18*a*R can be simultaneously controlled. The power 48*a* required to operate the ASC system 10*a* is preferably derived from a main power bus or the aircraft. The ASC system 10*b* is preferably installed in combination with passive mounts 56*a*L, 56*a*L' and 56*a*R and 56*a*R' which are attached between the yokes 32*a*L and 32*a*R and the engines 18*a*L and 18*a*R. AVAs 40*a*L, 40*b*L, 40*d*L, 40*e*L and 40*a*R, 40*b*R, 40*d*R, 40*e*R are preferably devices which provide active forces along a single linear axis only.

Figure 3B:
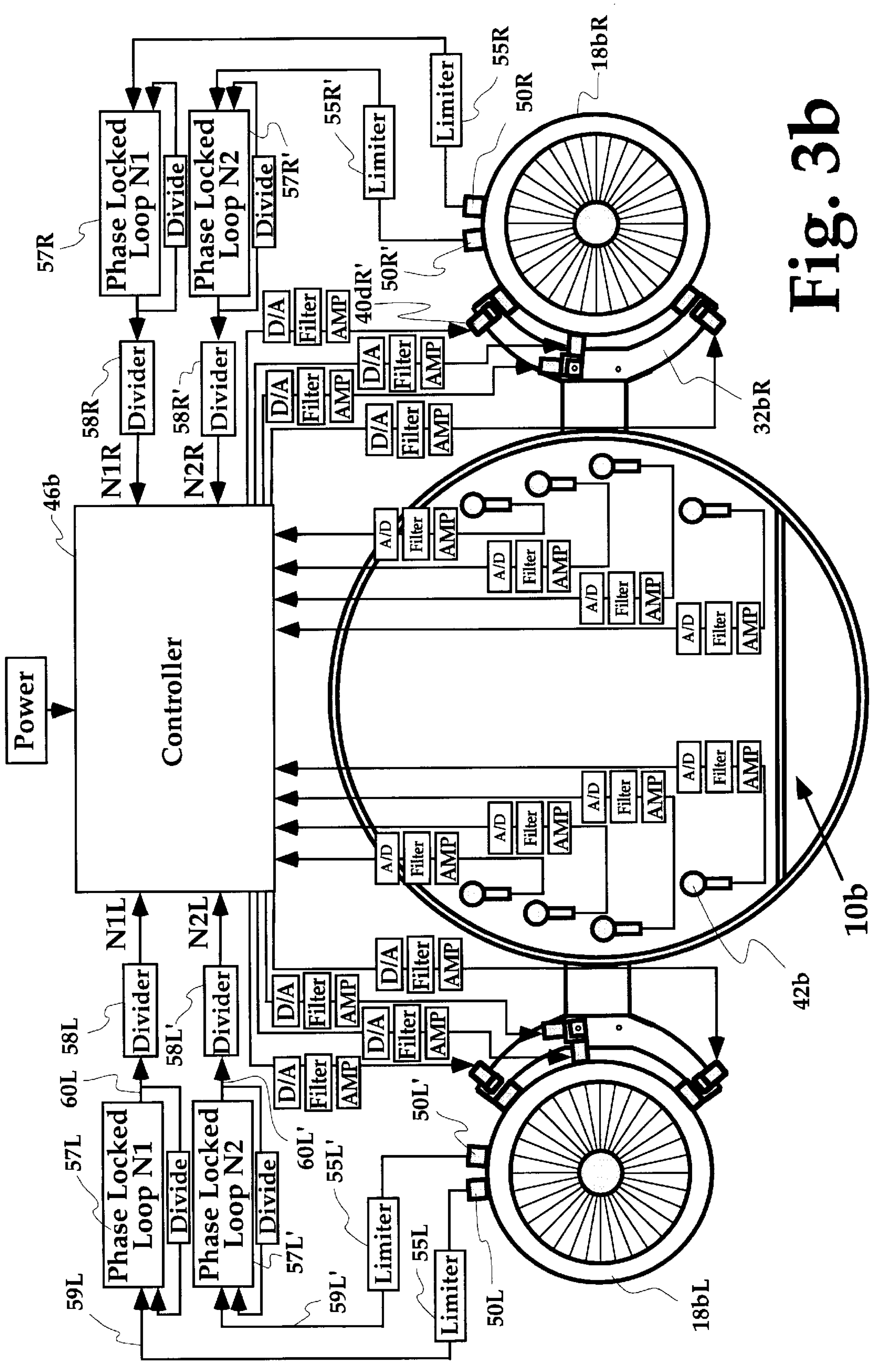
FIG. 3*b* is a schematic forward-looking view of a second embodiment of the present invention ASC system including AVAs attached to the yoke of an aircraft wherein reference signals are derived from multiple tachometer reference sensors.

FIG. 3*b* illustrates another embodiment of ASC system 10*b*. This ASC system 10*b* is similar to that described with reference to FIG. 3*a* except that the input (reference) signal is derived from multiple tachometer sensors 50L, 50L', 50R, and 50R', two associated with each engine 18*b*L and 18*b*R. For example, sensor 50L and sensor 50R pick up signals indicative of N1L and N1R rotations of the left and right engines 18*b*L and 18*b*R, respectively.

The signal indicative of N1L and N1R (and also N2L and N2R) are actually signals indicative of a passage frequency of gear teeth members associated with the engine's fan assembly and must be adjusted by some rational number (a Gear Ratio (GR)) to arrive at a signal exactly correlated with N1L and N1R, i.e., the exact N1L and N1R signals. First, the raw signal indicative of the gear tooth passage frequency is preferably converted into a square wave via hysteresis operation. The signal is then reduced (clipped) by limiter 55L to cut off the peaks of the signal to a finite voltage level. That quasi-clipped signal in line 59L is fed into a Phase Locked Loop (PLL) 57L which locks onto the dominant rotational frequency relating to the fan gear tooth passage frequency and preferably includes a multiplication factor (derived from a divide step in the comaparator path of the PLL). Next that signal output from the PLL 57L in line 60L is preferably divided via divider 58L by some integer multiple. By way of example, the N1L signal may be first multiplied in PLL 57L by an integer number and divided in divider 58L by an integer number. By way of example, the GR's for N1L and N2L are given by:

$GR_{N1}=47/23$ $GR_{N2}=35/12$ and N1L, N2L frequencies are given by:

$N1L=GR_{N1}\times$Raw Signal at 59L $N2L=GR_{N2}\times$Raw Signal at 59L'

Likewise, the N2L signal is derived from tachometer sensor 50L' which is limited by limiter 55L', passed through PLL 57L' to provide a multiplied signal in line 60L', and divided by divider 58L' to provide the exact N2L signal. Similar limiters 55R and 55R', PLLs 57R and 57R', and dividers 58R and 58R' are provided for deriving the N1R and N2R signals. It should be recognized that if a one-to-one signal is available, then the divide step in the PLLs and the dividers are not needed.

All of the processing and memory storage operations relating to providing output signals to the AVAs is preferably accomplished within the digital electronic controller 46*b*.

Figure 3C:
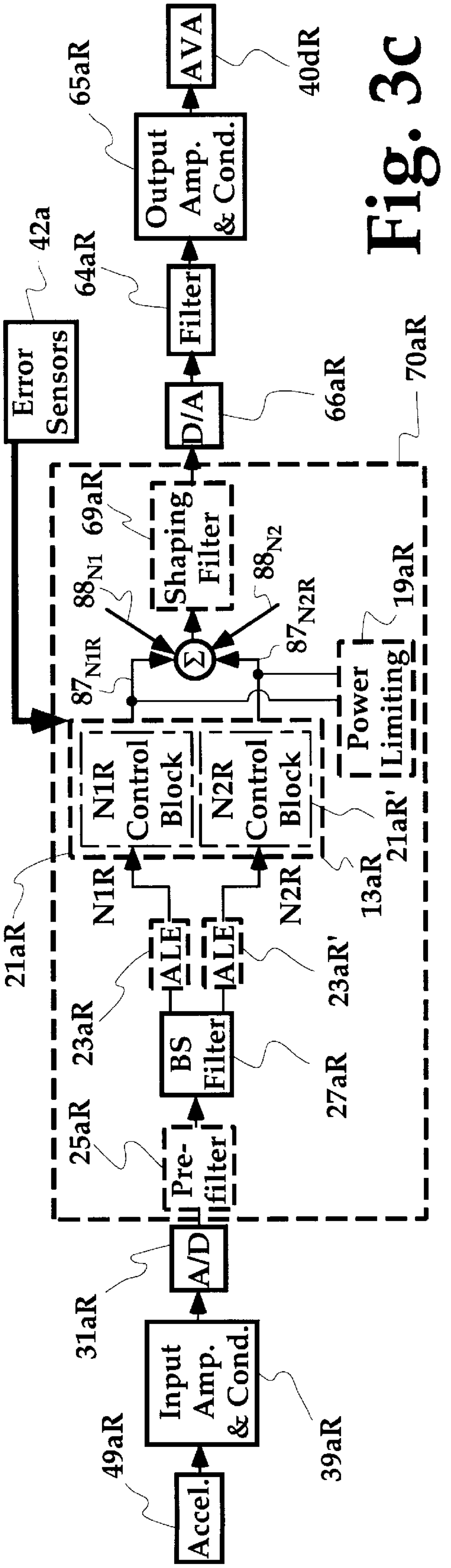
FIG. 3*c* is a block diagram of the input, control, and output components related to driving one of the AVAs for controlling vibration of the right yoke in the FIG. 3*a* embodiment at multiple frequencies.

With reference to FIG. 3*c*, the input, output, and control components associated with driving a single AVA, such as AVA 40*d*R located on right yoke 32*a*R (FIG. 3*a*) are described. Although, only the components for AVA 40*d*R on the right yoke 32*a*R are described, it should be understood that like elements would be associated with each of the other AVAs on the right yoke 32*a*R as well as all AVAs on the left yoke 32*a*L. An accelerometer 49*a*R provides the input signal indicative of N1R and N2R. That input signal is conditioned and amplified by input amp & conditioner 39*a*R. A/D converter 31*a*R transforms the signal into digital form. Box 70*a*R indicates the steps taking place within the digital controller 46*a* (FIG. 3*a*) and which preferably take place in software.

An optional digital prefiltering step including prefilter 25*a*R (digital low pass, high pass, band pass or combinations thereof) may be used to further refine the input signal. Next, the signal containing N1R and N2R components is separated into its N1R and N2R components using a digital band separation filter 27*a*R which may also comprise digital low pass, high pass, band pass filters, or combinations thereof. Preferably, a low pass is used to derive the N1R signal and a high pass is used to derive the N2R signal. The cutoff frequency for each is in between N1R and N2R. Optional ALEs 23*a*R and 23*a*R' can be included to further enhance/refine the N1R and N2R reference signals. ALEs are described in U.S. patent application Ser. No. 08/673,458 filed Jun. 17, 1996 by Southward et al. entitled "Active Noise Or Vibration Control (ANVC) System And Method Including Enhanced Reference Signals."

Each signal indicative of N1R and N2R is convolved with the appropriate control filter within a N1R control filter block 21*a*R and with the appropriate control filter within a N2R control filter block 21*a*R', respectively, to produce individual control filter output signals at the N1R and N2R frequencies. The blocks of control filters are within the adaptive control 13*a*R. It should be understood that error sensor information from the plurality of error sensors 42*a* are provided to the adaptive control 13*a*R including N1R control filters 21*a*R and N2R control filters 21*a*R'. Although, band separated control is shown, it should be understood that both the N1R and N2R signal information could be passed directly into the control filter block as a superimposed signal and convolved with a standard FIR, IIR filter, or the like.

In FIG. 3*c*, the outputs $\mathbf{87}_{N1R}$ and $\mathbf{87}_{N2R}$ from each control filter block 21*a*R and, 21*a*R' are summed together to derive the raw digital output signal to the AVA 40*d*R. Likewise, output signals from other control filters (for example, indicative of higher order tones or contributions from left adaptive control) may also be summed at $\mathbf{88}_{N1}$ and $\mathbf{88}_{N2}$. Optional power limiting 19*a*R may be included to prevent overdriving of the AVA 40*d*R. Power limiting is described in U.S. patent application Ser. No. 08/260,660 to Southward et al. filed Jun. 16, 1994 entitled "Active Control of Noise and Vibration." The combined output signals are then shaped by optional shaping filter 69*a*R to normalize the control signals provided to the AVA 40*d*R. The shaping filter is described in U.S. patent application Ser. No. 08/553,186 to Steenhagen, Southward, and Delfosse filed Nov. 7, 1995 entitled "Frequency Selective Active Adaptive Control System." The output signal is then transformed into analog form by the D/A converter 66*a*R, filtered by analog output filter 64*a*R, and finally amplified and conditioned by output amp and conditioner 65*a*R to produce the dynamic drive signal to dynamically drive the AVA 40*d*R.

Figure 3D:
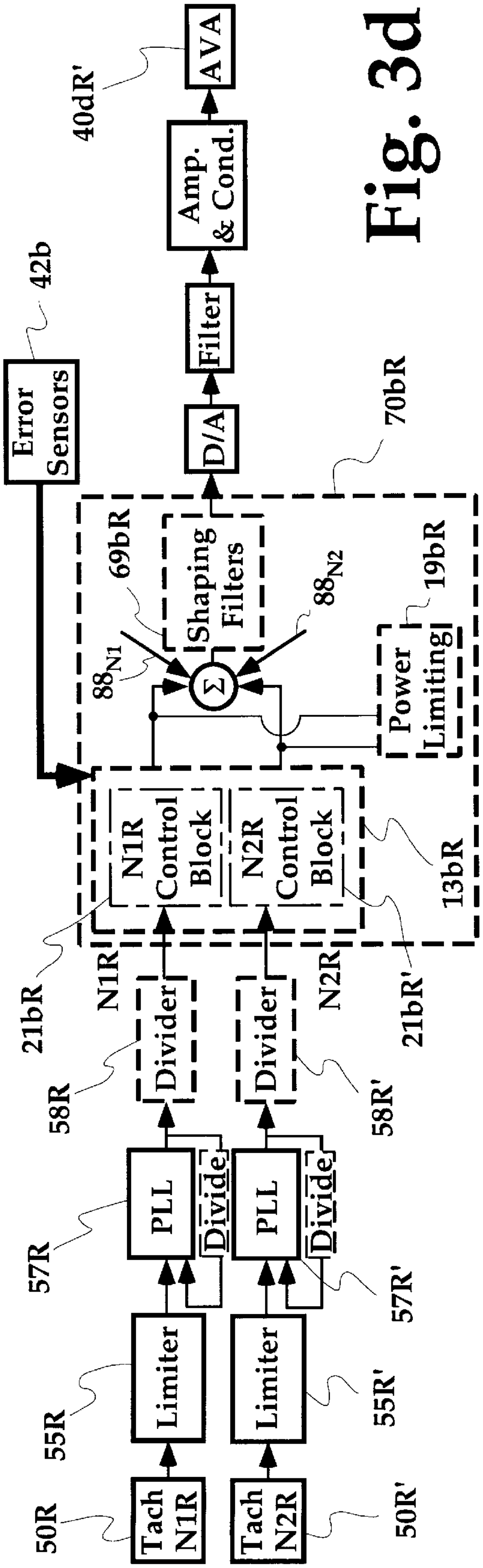
FIG. 3*d* is a block diagram of the input, control, and output components of the FIG. 3*b* embodiment.

With reference to FIG. 3*d*, the input, output, and control components associated with driving AVA 40*d*R' located on right yoke 32*b*R (FIG. 3*b*) are described. The components are similar to the previous embodiment, except for the input components. Tachometer signals from tachometer sensors 50R and 50R' are limited via limiters 55R, 55R'. The signal is then locked onto using PLLs 57R and 57R' which preferably include a divide step to multiply up the input signal frequency. The signal is then divided by divider 58R and 58R' to derive signals correlated with the N1R and N2R disturbance.

The reference signals indicative of N1R and N2R are then provided to adaptive control 13*b*R which includes control filter blocks 21*b*R and 21*b*R'. Elements within box 70*b*R are preferably implemented in software. Error information is provided via the plurality of error sensors 42*b*. It should be understood the error information from all error sensors may be provided to the adaptive control for the right yoke 32*b*R in the fully-coupled case. Likewise, output signals from other control filters may also be summed at $\mathbf{88}_{N1}$ and $\mathbf{88}_{N2}$. However, it is preferable to decouple the right and left engines, such that the adaptive control 13*b*R only receives reference signal information from the right engine and error information from the error sensors most strongly coupled to the AVA 40*d*R'. This decoupling or partitioning will be more fully described with reference to FIGS. 6*a*–6*c*.

Figure 3E:
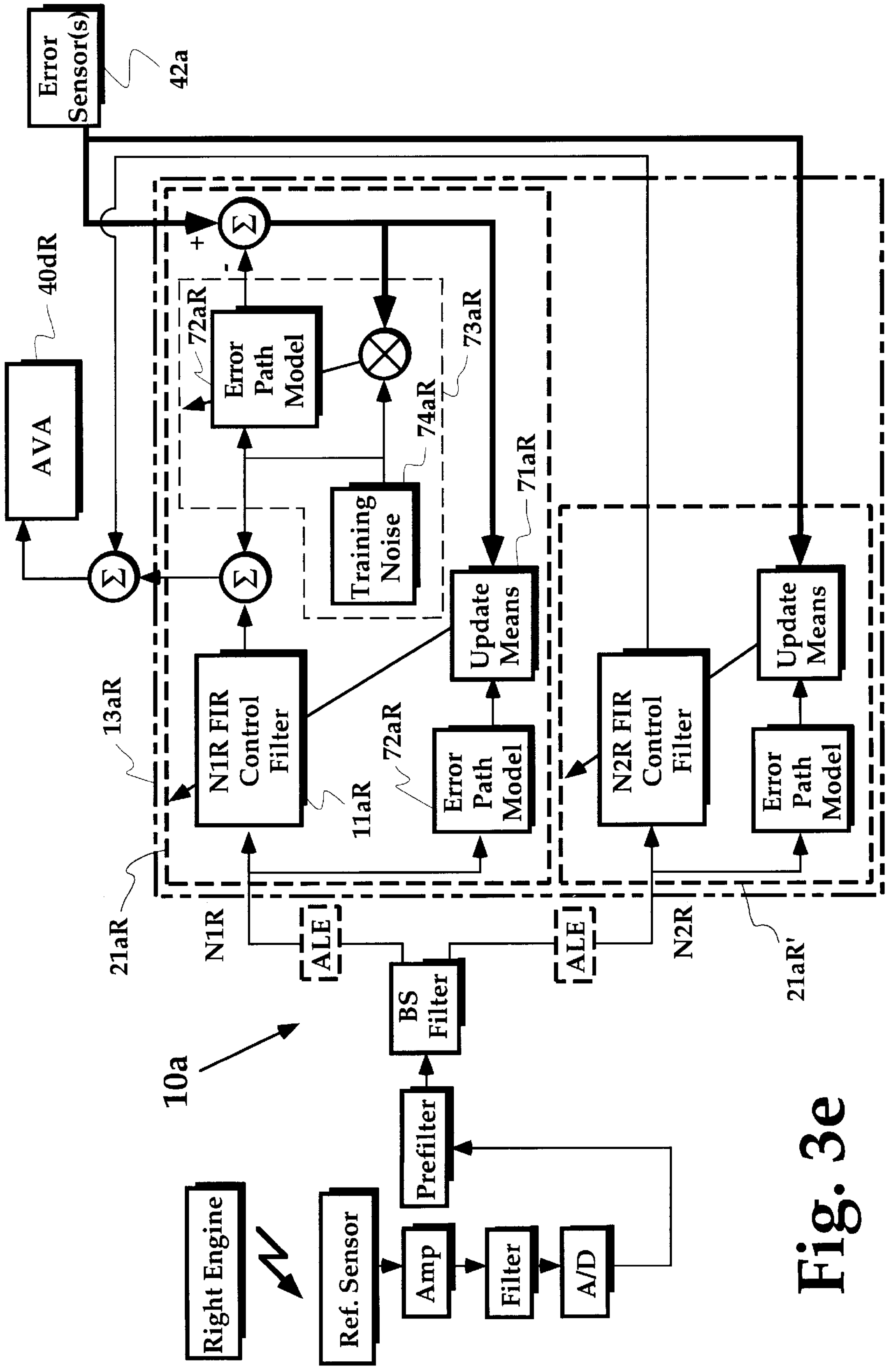
FIG. 3*e* is a further refined block diagram of one particular type of adaptive control useful for controlling the AVAs in the FIG. 3*a* embodiment.
Figure 3F:
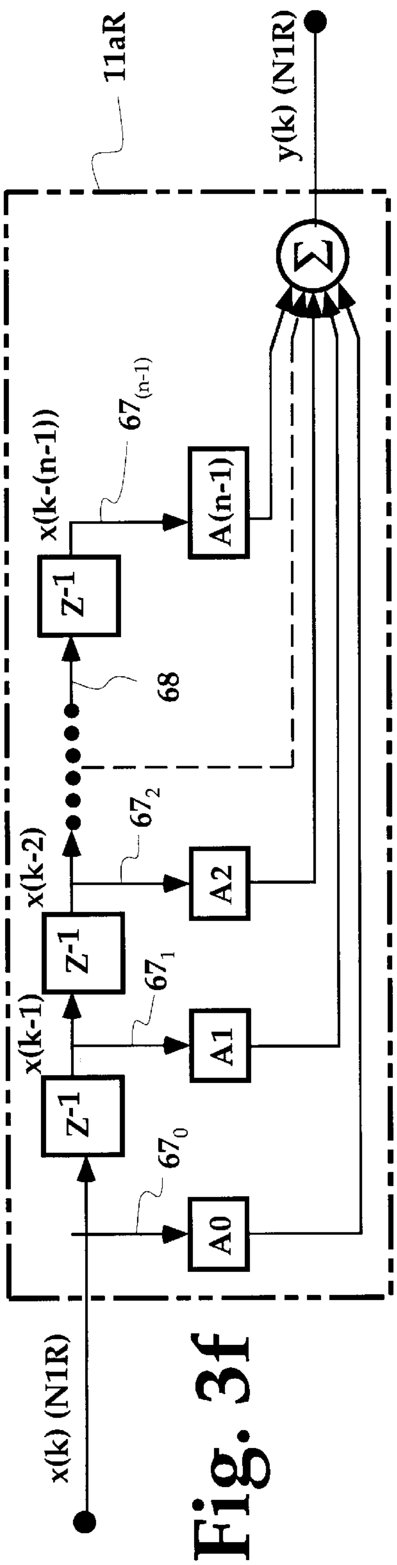
FIG. 3*f* is a block diagram of one possible control filter configuration (e.g. FIR) which could be used with the FIG. 3*a* or 3*b* embodiment.
Figure 3G:
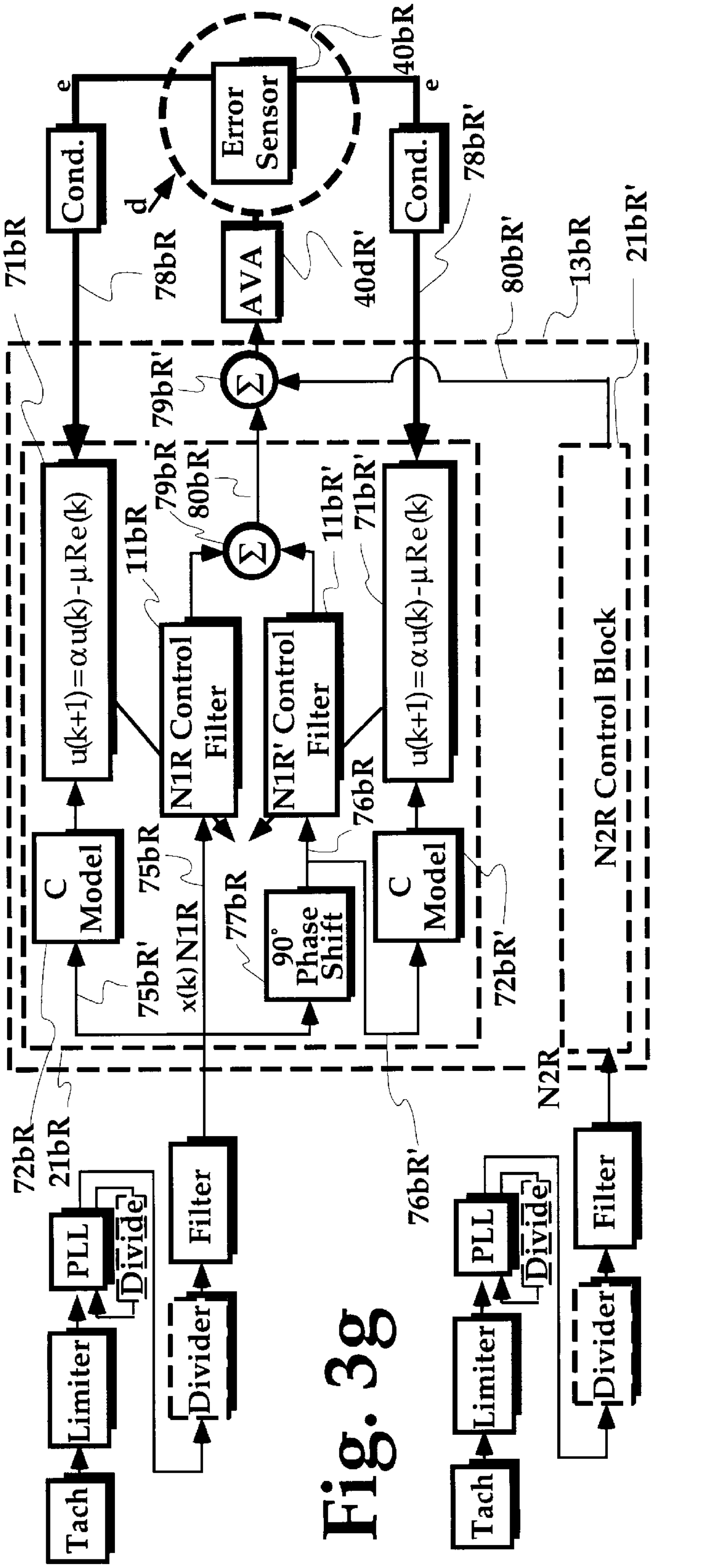
FIG. 3*g* is a block diagram of another possible adaptive control which could be used in the FIG. 3*a* or 3*b* embodiment.
Figure 3H:
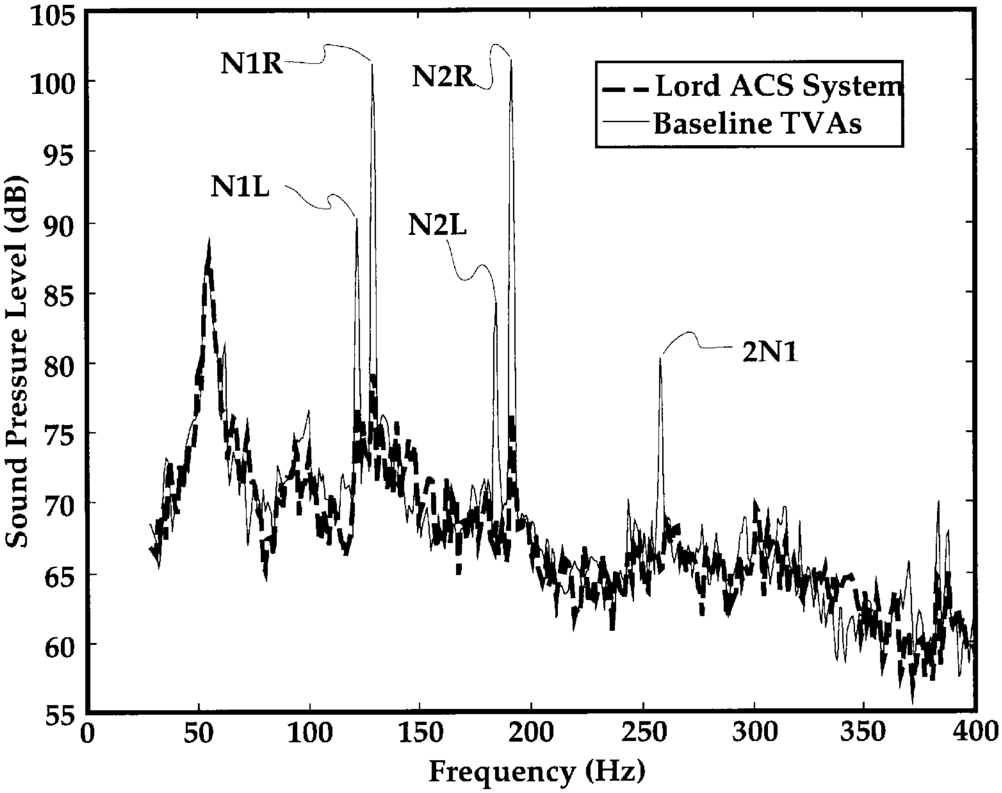
FIG. 3*h* is a graphical plot illustrating the reductions of the N1R, N1L and N2R, N2L tones by the present invention ASC system including AVAs attached to the yoke as compared to a baseline system which includes only passive TVAs attached to the yoke.
Figure 3I:
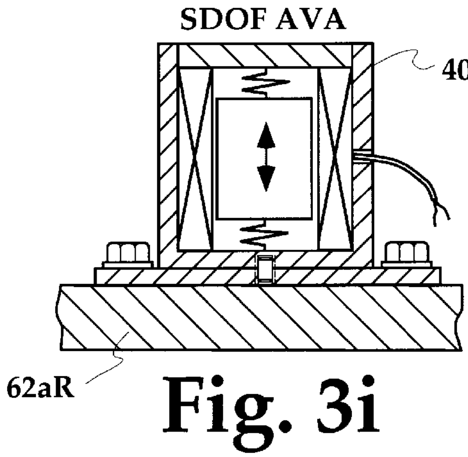
FIG. 3*i* is a cross-sectioned side view of a SDOF AVA.
Figure 3J:
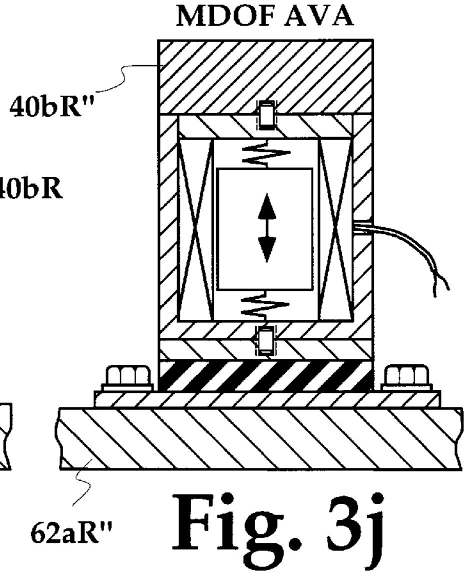
FIG. 3*j* is a cross-sectioned side view of a MDOF AVA.

FIG. 3*e* illustrates the details of one preferred control architecture for the present invention ASC system 10*a*. In particular, within the N1R control block 21*a*R in the adaptive control 13*a*R is an FIR control filter configuration including a preferable FIR control filter 11*a*R which is preferably updated via a preferably adaptive gradient descent update means. Preferably, Filtered-x Least Mean Square (LMS) method is used to update the weights of the N1R control filter 11$a$R. The update means 71$a$R preferably performs the weight update process based upon information derived via convolving the N1R signal with an error path model 72$a$R and the error information from plurality of error sensors. A description of this control architecture may be found in U.S. patent application Ser. No. 08/673,458 filed Jun. 17, 1996 by Southward et al. entitled "Active Noise Or Vibration Control (ANVC) System And Method Including Enhanced Reference Signals."

The control block may include system identification 73$a$R for deriving the error path model 72$a$R. The system ID can be performed in either an on-line or off-line fashion. The system ID involves obtaining the error path model, i.e., the transfer function between each error sensor-AVA pair. Preferably, the ID occurs by inducing low-level known and uncorrelated training noise 74$a$R into the ASC system 10$a$ to derive the response thereto. The error path model is then copied and used for all update means. A further description of a preferable system identification method can be found in U.S. Pat. Nos. 4,677,676 and 4,677,677 to Eriksson. Identical elements are included within the N2R control filter.

FIG. 3$f$ describes a conventional FIR transversal filter, for example, the transversal filter is the preferable form for the N1R control filter 21$a$R shown in FIG. 3$e$. Transversal control filters, e.g. 21$a$R have multiple taps $\mathbf{67}_0$, $\mathbf{67}_1$, $\mathbf{67}_2$, . . . , $\mathbf{67}_{n-1}$ which represent various values of x(k), in this example indicative of the N1R tone. The taps extract various x values, such as x(k), x(k−1), x(k−2) . . . , x(k(n−1)) at successive unit increments from tapped delay line 68. Each delay block $Z^{-1}$ represents a unit sample tap delay. Weights $A_0$, $A_1$, $A_2$, . . . , $A_{n-1}$ are individually adjusted in an adaptive fashion to accomplish the adaptation of the drive signal to each of the AVAs. The output signal y(k) from the transversal FIR filter is approximately governed by the following equation:

$$y(k)=x(k)\,A_0+x(k-1)\,A_1+x(k-2)\,A_2+x(k-3)\,A_3+\ldots+x(k-(n-1))\,A_{n-1}$$

where:
y(k)=output signal from control filter
n=number of taps
$A_0$–$A_{n-1}$=control filter weights
k=unit step As was indicated above, each weight $A_0$ through $A_{n-1}$ is preferably updated by a filtered-x LMS method according to the equation:

$$A_0(k+1)=A_0(k)+\mu e_k R(k)$$

where:
$\mu$=convergence coefficient
$e_k$=error signal information
R(k)=filtered-x information Updates to the weights $A_0$ through $A_{n-1}$ can be accomplished in an on-line fashion and as fast as practicable.

FIG. 3$g$ illustrates another possible control architecture which is useful in controlling an ASC system, such as the ASC system 10$b$ and was described with reference to FIG. 3$b$. Alternatively, it could also be used with other embodiments described herein. Input signals indicative of N1R and N2R are provided to adaptive control 13$b$R, and to control filter blocks 21$b$R and 21$b$R' included therein. The structure of the N1R block 21$b$R will be described. It should be understood that similar structures would be employed for the N2R block 21$b$R' and the control blocks for the left engine. The input signal N1R is provided to the control block 21$b$R and is separated into its in-phase and out-of-phase components, i.e., its quadrature components (sine and cosine-like waves) in lines 75$b$R and 76$b$R, respectively. The out-of-phase component signal is provided by a 90° phase shift step in 90° phase shift block 77$b$R. The in-phase and out-of-phase components are provided to N1R and N1R' control filters 11$b$R and 11$b$R', to be convolved respectively therewith. The weights of the adaptive filters are preferably adjusted via an update method, in particular, an adaptive gradient descent method, such as a Filtered-x LMS method, in adaptive update means 71$b$R and 71$b$R'. This type of control where the reference signals are split into quadrature components and separately convovled with control filters is hereinafter referred to as a "quadrature-type control."

The in-phase and out-of-phase component signals 75$b$R' and 76$b$R' are preferably also input to the C models 72$b$R and 72$b$R' (otherwise known as error path models) and convolved therewith to produce vector R, which is used in the adaptive weight update method along with the error signal information e(k) in lines 78$b$R and 78$b$R' from the plurality of error sensors 42$b$R. The output from each control filter 11$b$R and 11$b$R' are summed together to produce the N1R drive signal to AVA 40$d$R'. The N2R drive signal in line 80$b$R' is produced via similar means as is described for N1R control block 21$b$R and is summed together at adder 79$b$R' with the N1R drive signal in line 80$b$R to produce the combined drive signal to dynamically drive AVA 40$d$R' at both frequencies thereby controlling noise and/or vibration within the cabin at both frequencies associated with N1R and N2R. It should be understood that other variations in control architecture are possible, such as Infinite Impulse Response (IIR) are also possible.

FIG. 3$h$ illustrates a frequency domain graphical plot of the actual performance comparison of a McDonnell Douglas DC-9-30 aircraft with JT8D engines including the baseline system (thin solid line) having yoke-attached passive TVAs (4 per engine) as compared to the novel ASC system 10$b$ (thick dotted line) of the present invention. As is demonstrated, the sound pressure levels at the N1L, N2L and N1R, N2R are reduced significantly. In this case, even the tone at 2N1, which is thought to be due to structural nonlinearities, is reduced. The results were from a ground test with the left engine at 85% N1 power and the right engine at 90% N1 power. The 90% N1 would be comparable to a high power cruise condition of the aircraft. Separation of the right and left engine frequencies during testing facilitated demonstration of reductions in tones produced by both right and left engines. The data represents the results obtained at the location of a particular aft seat location at head height within the aft cabin and represents approximately a 25 dB reduction at the N2L tone and approximately 23 dB reduction at the N1L tone. Average results were somewhat lower, but generally in the range of 15–20 dB. Notably, nowhere in the cabin was the sound pressure level perceptibly increased. Further, even though there were only error sensors in the aft portion of the cabin, noise in the front portion of the cabin was also reduced.

For comparison purposes and help in understanding the data, it should be recognized that a halving of the sound pressure level occurs at 6 dB, reduction by a factor of 4 occurs at 12 dB, reduction by a factor of 8 occurs at 18 dB, and reduction by a factor of 16 occurs at 24 dB. Therefore, it should be recognized that a reduction of 25 dB represents a 94% reduction in tonal sound pressure level and is very recognizable by the passenger.

FIG. 3$i$ and FIG. 3$j$ represent cross-sectional views of AVAs, for example a Single Degree Of Freedom (SDOF) AVA 40$b$R and an alternative Multiple Degree Of Freedom (MDOF) configuration 40*b*R" for attachment to yoke 32*a*R via brackets 62*a*R in the ASC system 10*a*. The details of the MDOF AVAs can be found in WO 96/12121 by Schmidt et al. entitled "Active Systems and Devices Including Active Vibration Absorbers." In particular, the AVAs include one or more masses which can be preferably tuned to provide one or more resonant frequencies which substantially coincide with an operating condition and an active element therein for dynamically driving said one or more masses along, for example, a single defined axis A—A. It should be understood that the AVAs are preferably uni-directional and produce active (real-time) vibrational forces along a defined axis and their produced vibration can be changed in both phase and magnitude.

FIG. 4*a* illustrates the preferred location of AVAs in the ASC system 10*a* on the yoke 32*a*R which attaches to the right engine 18*a*R as was described with reference to FIG. 3*a*. Although, the right yoke 32*a*R is described in detail, it should be understood that the left yoke 32*a*L (FIG. 3*a*) would preferably be fitted with like ASC components. The yoke 32*a*R preferably attaches to the right engine 18*a*R via passive front mounts 56*a*R and 56*a*R' which include apertures 36*a* and 36*a* formed therein, respectively, for receiving attachment members 29*a* and 29*a*', such as bolts or the like. Preferable passive aft mount which attaches the aft portion of engine to the aft pylon is not shown. Generally, the AVAs attach, at various locations, to the yoke 32*a*R which, in turn, attaches by way of yoke bolts 34*a*R and 34*a*R' to the outboard portion of the spar 38*a*R at the yoke's base portion 35*a*R. The yoke 32*a*R and spar 38*a*R collectively comprise the pylon structure 28*a*. The pylon structure 28*a*R attaches between the engine 18*a*R and the fuselage 20*a* and comprises the mechanical transmission path for vibration transmission to the fuselage 20*a*.

Fuselage 20*a* preferably includes stiffening means such as stringers 22*a* and stiffening ring frames 24*a*, for lateral and hoop-wise stiffening, and may include an aft bulkhead 26*a* with optional stiffening struts 30*a* attached thereto. As illustrated, five (5) AVAs are shown in this side view of the ASC system 10*a*. Two AVAs, 40*e*R and 40*d*R which are preferably Single Degree Of Freedom (SDOF) AVAs and are preferably attached adjacent to the terminal end portions 33*a* and 33*a*' of yoke 32*a* by end brackets 61*a* and 61*a*'. Preferably, the SDOF AVAs 40*e*R and 40*d*R at terminal end portions 33*a* and 33*a*' are tuned to have a resonant frequency fn1 which substantially coincides with the most dominant N2R frequency (generally standard cruise frequency). By way of example, and not to be considered limiting, if the N2R cruise frequency were about 173 Hz, the AVAs 40*e*R and 40*d*R would be tuned such that their resonant frequencies fn1 would be just below the standard cruise frequency (tuned to about 170 Hz—approx. 98% of the most common operating frequency to be controlled).

Preferably, the terminally-positioned AVAs 40*e*R and 40*d*R are oriented to provide substantially radially-acting dynamic forces, as is indicated by arrows labeled RV and RV'. It was discovered by the inventors that radial orientation and tuning to substantially coincide with N2R provides efficient and enhanced control of N2R vibrations of the right engine 18*a*R which are transmitted into the yoke 32*a*R. Optionally, the AVAs 40*e*R and 40*d*R may be MDOF AVAs which exhibit multiple resonant frequencies fn1 and fn2 which may be tuned to substantially coincide with both the N1R and N2R frequencies. MDOF AVAs can be found in WO 96/12121 by Schmidt et al. entitled "Active Systems and Devices Including Active Vibration Absorbers."

Attached at the base portion 35*a*R of yoke 32*a*R are AVAs 40*a*R and 40*b*R which are preferably SDOF AVAs, which are preferably tuned such that their resonant frequencies fn1 substantially coincide with the most common or predominant N1R frequency. Although, they will be driven at both N1R and N2R, tuning their passive resonances fn1 to substantially coincide with N1R will provide more efficient control of N1R vibrations. By way of example, and not to be considered limiting, there are preferably four AVAs attached at, or adjacent to, the base portion 35*a*R. Space permitting, they may be equally positioned at yoke bolts 34*a*R and 34*a*R'. Preferably, two AVAs are placed on each side of the yoke 32*a*R at the base portion 35*a*R, one at each bolt location. Preferably, the AVAs act in a direction selected from the group consisting of the radial, tangential, or fore and aft directions (FIG. 5*a*).

AVA 40*b*R is shown acting substantially in the radial direction (directed toward the center of engine 18*a*R) as indicated by arrow RV" (radial vector) and is attached to the yoke 32*a*R via base bracket 62*a*R and yoke bolt 34*a*R. AVA 40*a*R is shown acting tangentially as is indicated by arrow TV (tangential vector, i.e., tangential to the radial vector) and may also be attached to yoke 32*a*R via bracket 62*a*R and yoke bolt 34*a*R. The other AVAs and their locations are described with reference to FIG. 5*a*. Optional AVA 40*c*R is shown oriented in a part radial-part tangential orientation as indicated by arrow RTV (radial-tangential vector) and is attached by bracket 62*a*R' and yoke bolt 62*a*R'. Additionally, AVAs located at the base portion 35*a*R may also be MDOF AVAs. Combinations of MDOF and SDOF AVAs may be desirable, as, in general, where space is available, a MDOF AVA will provide enhanced control of both N1R and N2R vibrations.

Figure 4B:
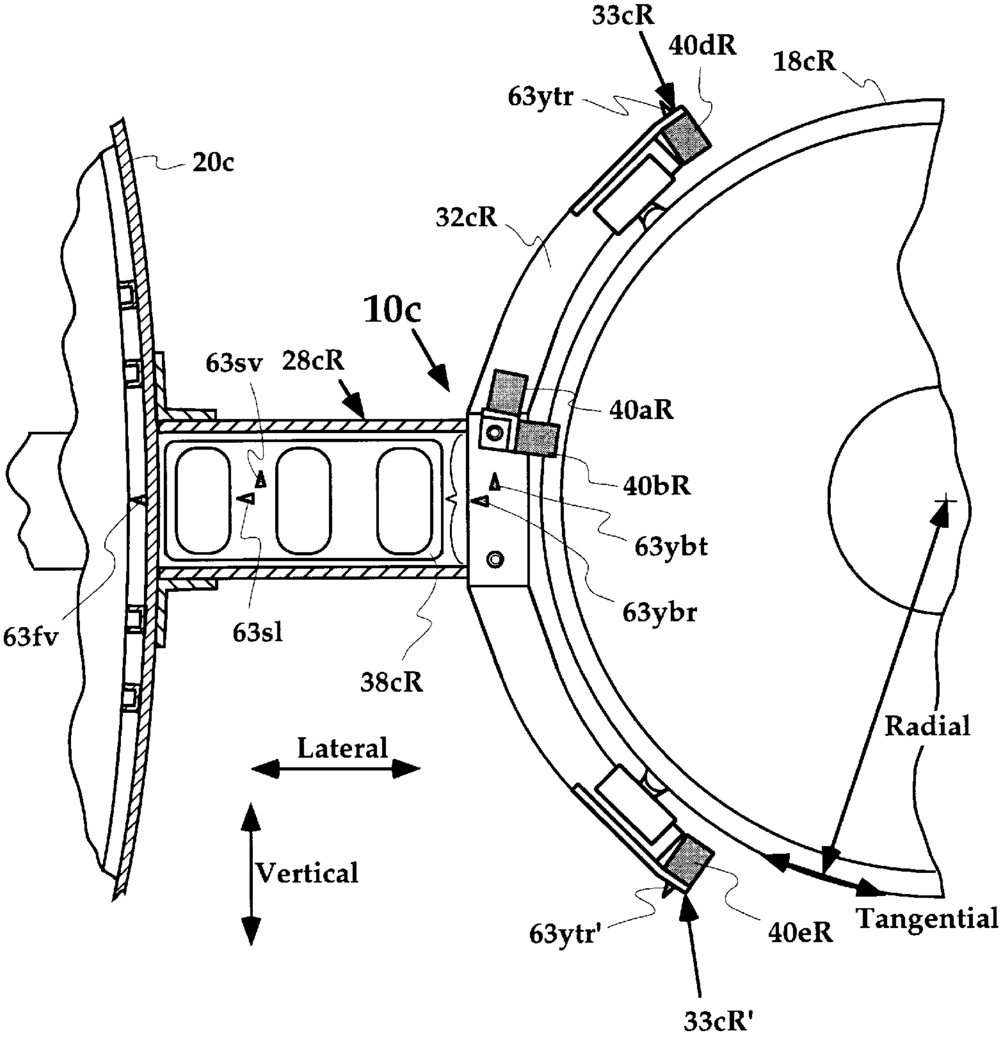
FIG. 4*b* is a detailed partial forward-looking schematic view of another embodiment of the present invention ASC system illustrating preferred locations of accelerometer error sensors.

FIG. 4*b* illustrates an forward-looking view of a portion of another embodiment of the ASC system 10*c*. In this embodiment, accelerometers located on the pylon structure 28*c*R are used as the error sensors in place of microphones located in the aircraft cabin. These accelerometers provide the residual error signals (indicative of vibration) for use in controlling the AVAs. Preferably, accelerometers 63*ytr* and 63*ytr*' are located at or near the terminal ends 33*c*R and 33*c*R' of yoke 32*c*R and are substantially collocated with the radially-acting AVAs 40*d*R and 40*e*R and provide radial acceleration information indicative of the residual vibration thereat. Likewise, accelerometers 63*ybt* and 63*ybr* provide measurements of the residual vibration of the base portion 38*c*R of the yoke 32*c*R in the tangential and radial directions, respectively. Preferably, accelerometers 63*ybt* and 63*ybr* are substantially collocated with tangentially-acting AVA 40*a*R and radially-acting AVA 40*b*R. Alternatively, or additionally, accelerometers, such as 63*sv* and 63*sl* may be placed on the spar 38*c*R to provide measurements of residual vibration in the vertical and lateral directions, respectively. Notably, placement of error sensors on the spar 38*c*R would require more elaborate error models as compared to collocation of the error sensors with the AVAs. Likewise, multiple accelerometers placed on the fuselage 20*c*, such as 63*fv*, may also be used to control the vibration of the fuselage 20*c* caused vibration of engine 18*c*R. Controlling the dominant modes of vibration that are coupled with the acoustic volume within the aircraft cabin is thought to control the acoustic noise produced therein.

FIG. 5*a* illustrates an forward-looking view of the ASC system 10*a*, less engines, illustrating the right and left yokes 32*a*L and 32*a*R (each of which is turned 90° aft for clarity, i.e., the fore and aft directions for each yoke are shown with arrows) with interconnection to the fuselage 20*a* indicated by heavy-dotted lines HD and HD'. The right hand yoke 32*a*R, and the locations of AVAs thereon, will be described in detail. It should be understood that the AVA numbers, attachments, locations, and directions of action on left hand yoke 32aL, as indicated by AVAs 40aL, 40bL, 40dL, 40eL, 40fL, and 40gL are preferably identical to that of the right hand yoke 32aR.

Shown on the right hand yoke 32aR is the first preferred configuration of AVAs. At the terminal end portions 33a and 33a' are located AVAs 40dR and 40eR which are preferably SDOF AVAs which act in a substantially radial direction and are preferably tuned to exhibit a resonant frequency substantially coinciding with the N2R rotational frequency of right engine 18aR (e.g. FIG. 4a). AVAs 40aR, 40bR, 40gR and 40fR attach at the base portion 35aR on opposite sides of yoke 32aR adjacent to the point of attachment of yoke 32aR to spar 38aR. Preferably, the base-portion-mounted AVAs are also SDOF AVAs and are preferably tuned such that each exhibits a natural frequency which substantially coincides with the N1R operating frequency.

Alternatively, where the space and weight considerations allow, Multiple Degree Of Freedom (MDOF) AVAs may be used and attached to the yoke 32aR. Optional AVA locations/directions are illustrated for optional AVAs 40hR and 40cR wherein the AVAs are directed to act substantially in a fore and aft direction (AVA 40hR) or in a direction having components of both the radial and tangential (AVA 40cR). In particular, it was discovered by the inventors that tuning the preferably at least four AVAs, 40aR, 40bR, 40gR and 40fR to have resonant frequencies that substantially coincide with N1R frequency is particularly effective at controlling N1R vibrations, which if transmitted to the spar 38aR, would be responsible for annoying N1R tones emerging in the aircraft cabin 44a. Although, the AVAs may be tuned to one particular frequency, it is desirable to actuate them at multiple frequencies (both N1R and N2R). For example, AVAs 40aR and 40gR are directed to act in substantially tangential directions and are preferably each tuned to exhibit natural frequencies substantially coincident with N1R, however, the AVAs 40aR and 40gR would also be driven at the N2R frequency, albeit they would be less effective at that frequency as if the AVA were tuned to have a natural frequency substantially coincident at N2R.

Furthermore, where MDOF AVAs can be used, they are preferably tuned to exhibit first and second resonant frequencies which substantially coincide with both N1R and N2R, and thereby both frequencies may be actuated to control vibration with improved efficiency. Likewise, AVAs 40bR and 40fR are directed to act in substantially radial directions and are preferably each tuned to exhibit natural frequencies substantially coincident with N1R. Alternatively, one of the tangential AVAs, such as 40gR may be replaced with fore-and-aft acting AVA, such as 40hR or a radial acting AVA, such as 40bR. For clarity, the Amp, filter and D/A or A/D converters as described with reference to FIG. 3a are collectively labeled cond. (short for conditioning).

Figure 5B:
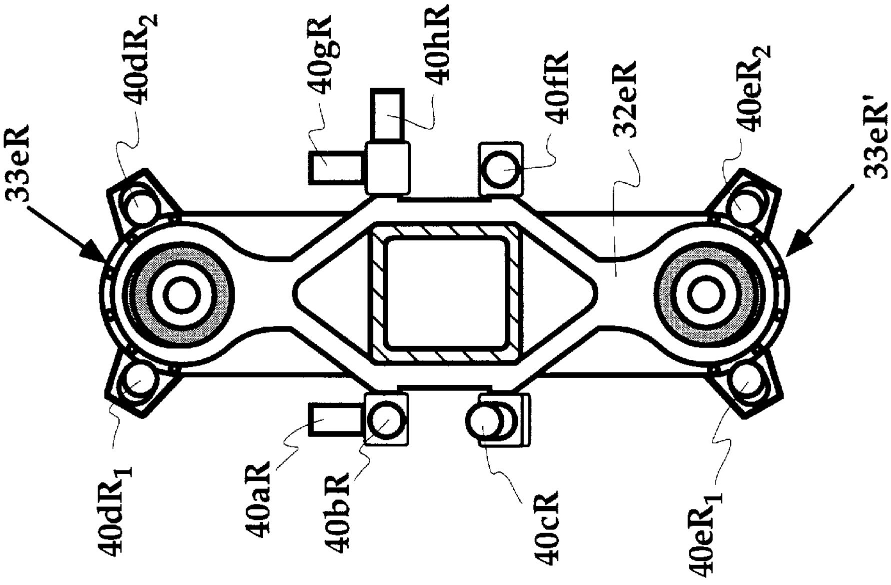
FIG. 5*b* is a schematic diagram of another embodiment illustrating locations/directions of a plurality of AVAs on the right yoke.
Figure 5C:
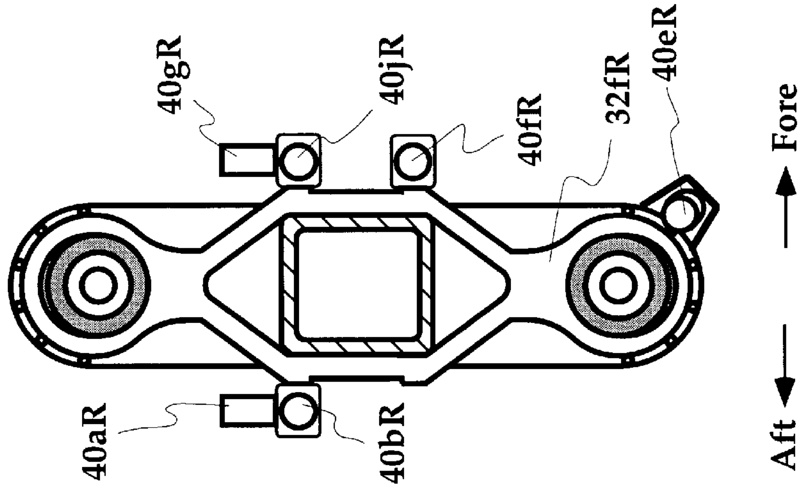
FIG. 5*c* is a schematic diagram of another embodiment illustrating preferred locations/directions of a plurality of AVAs.
Figure 5D:
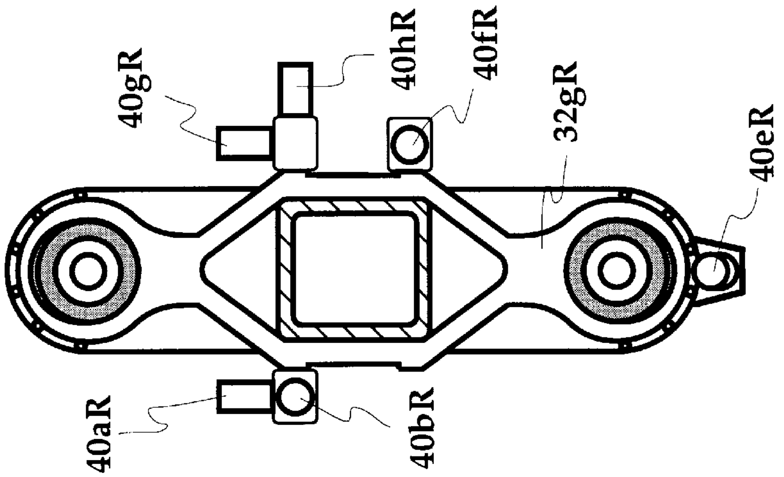
FIG. 5*d* is a schematic diagram of another embodiment illustrating preferred locations/directions of a plurality of AVAs.

FIG. 5b, FIG. 5c and FIG. 5d illustrate side views of the right yoke assemblies used on various alternative ASC systems similar to the ASC system 10a, except each illustrates on right yokes 32eR, 32fR, and 32gR different embodiments of preferred locations and directions of AVAs. On the yoke 32eR (shown in FIG. 5b) one preferred embodiment including AVAs 40aR, 40bR, 40d$R_1$, 40d$R_2$, 40e$R_1$, 40e$R_2$, 40fR, 40hR, and 40gR is illustrated. The main difference between the FIG. 5a configuration and the FIG. 5b configuration is that two AVAs, such as 40d$R_1$, 40d$R_2$, and 40e$R_1$, 40e$R_2$, are located at each of the terminal ends 33eR and 33eR' of the yoke 32eR. These are preferably SDOF AVAs, preferably act in a substantially radial direction, and are preferably tuned to exhibit natural frequencies substantially coincident with N2R. Illustrated on the right yoke 32fR is another embodiment including another configuration of AVAs 40aR, 40bR, 40eR, 40fR, 40gR, and 40jR. Illustrated on the right yoke 32gR is another embodiment including another configuration of AVAs 40aR, 40bR, 40eR, 40fR, 40gR, and 40hR. It was discovered experimentally by the inventors that the FIG. 5b configurations of AVAs yields particularly effective cancellation of noise within the cabin. Furthermore, it is anticipated that the preferred configurations of FIG. 5c and 5d will provide substantially equivalent vibration control results as compared to the FIG. 5b configuration with less AVAs required.

Figure 6A:
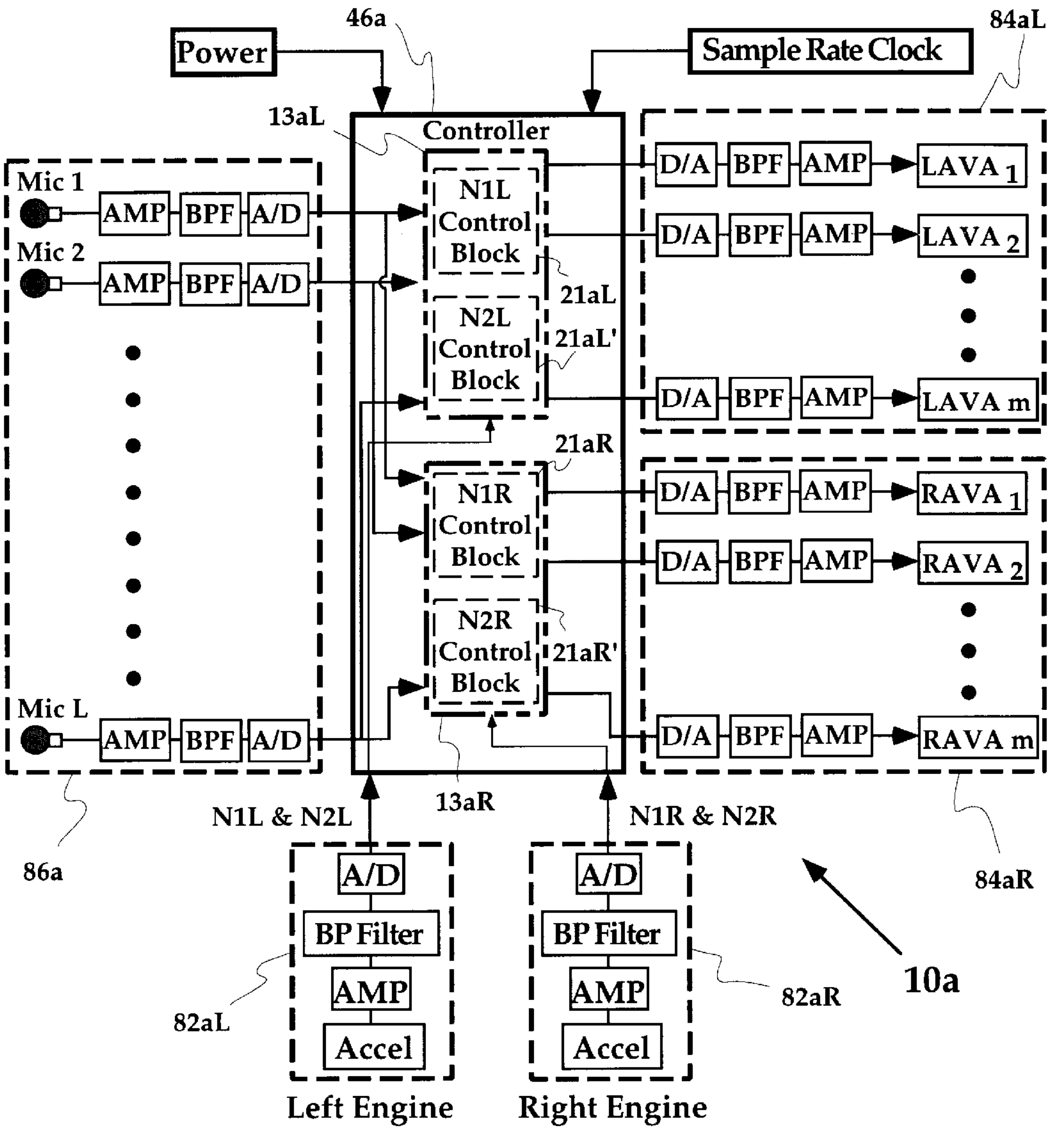
FIG. 6*a* is a schematic block diagram of the FIG. 3*a* embodiment of the present invention ASC system.

FIG. 6a illustrates a block diagram of the ASC system 10a and illustrates the partitioning/decoupling between the right and left side AVA control. The system 10a includes left engine reference signal generating means 82aL, right engine reference signal generating means 82aR, each for providing the signals indicative of N1L, N2L and N1R, N2R to the controller 46a. Within controller 46a are left adaptive control 13aL and right adaptive control 13aR for providing adapted output signals to the right AVA bank 84aR (including m number of right AVAs ($RAVA_1$ through $RAVA_m$)) and left AVA bank 84aL (including m number of left AVAs ($LAVA_1$ through $LAVA_m$)). Included within left and right adaptive control 13aL and 13aR are N1R, N2R and N1L, N2L control blocks 21aR and 21aR' and 21aL and 21aL' which include the adaptive filters. Error sensor information from error signal generating means 86a including L number of microphones within the cabin are provided to both the right and left adaptive control 13aL and 13aR. It should be understood that in the reference sensor partitioned case, left engine reference signal generating means 82aL is provided only to be used in the left adaptive control 13aL for driving the left AVA bank 84aL and right engine reference signal generating means 82aR is provided only to be used in the right adaptive control 13aR for driving the right AVA bank 84aR. Notably, error sensor information from error signal generating means 86a is used in all control blocks in this embodiment.

Figure 6B:
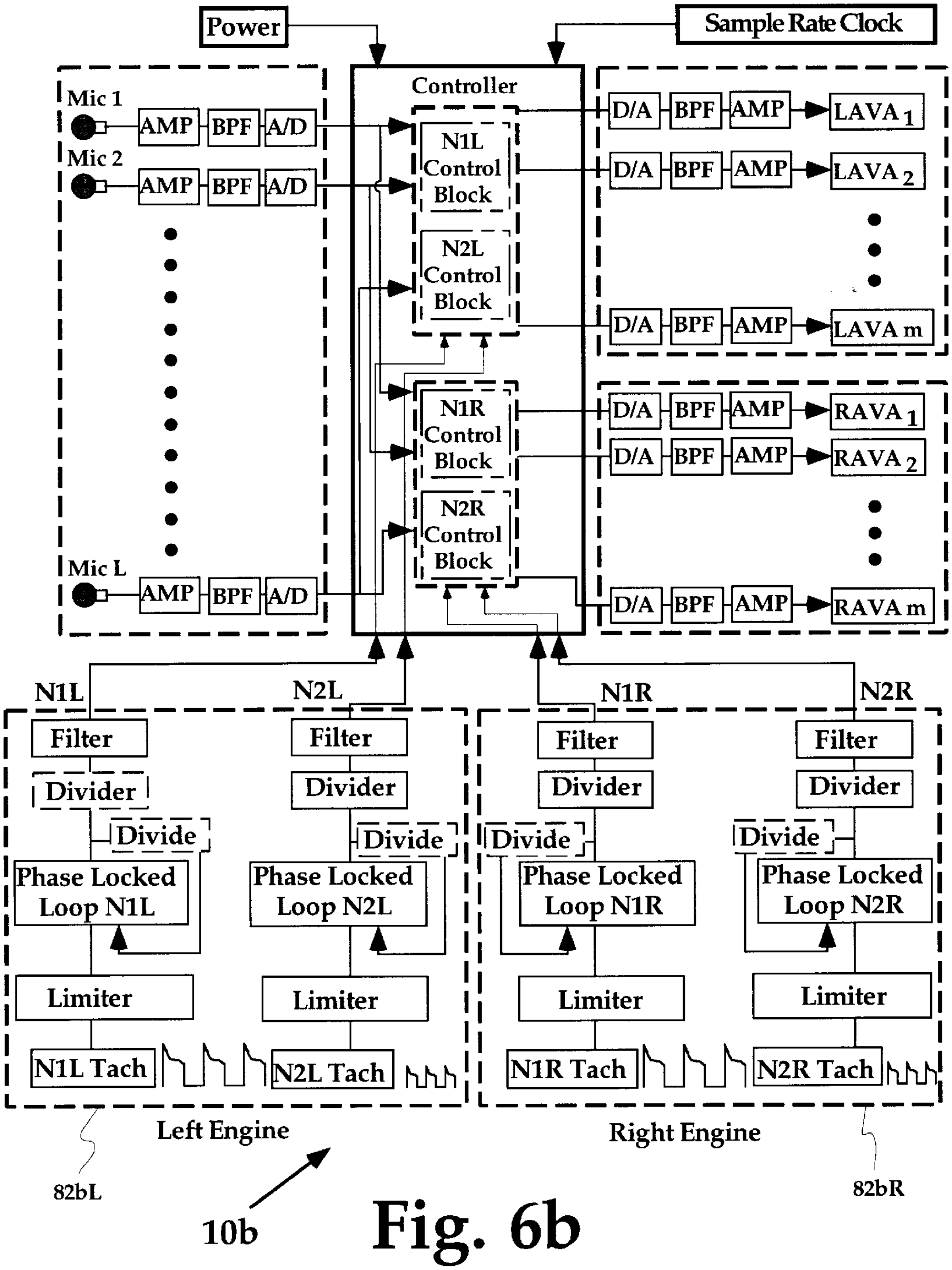
FIG. 6*b* is a schematic block diagram of the FIG. 3*b* embodiment of the present invention ASC system.

FIG. 6b illustrates a block diagram of the ASC system 10b. It is substantially similar to the system described with reference to FIG. 6a, except that the reference signal generating means 82bL and 82bR comprise tachometer sensors.

Figure 6C:
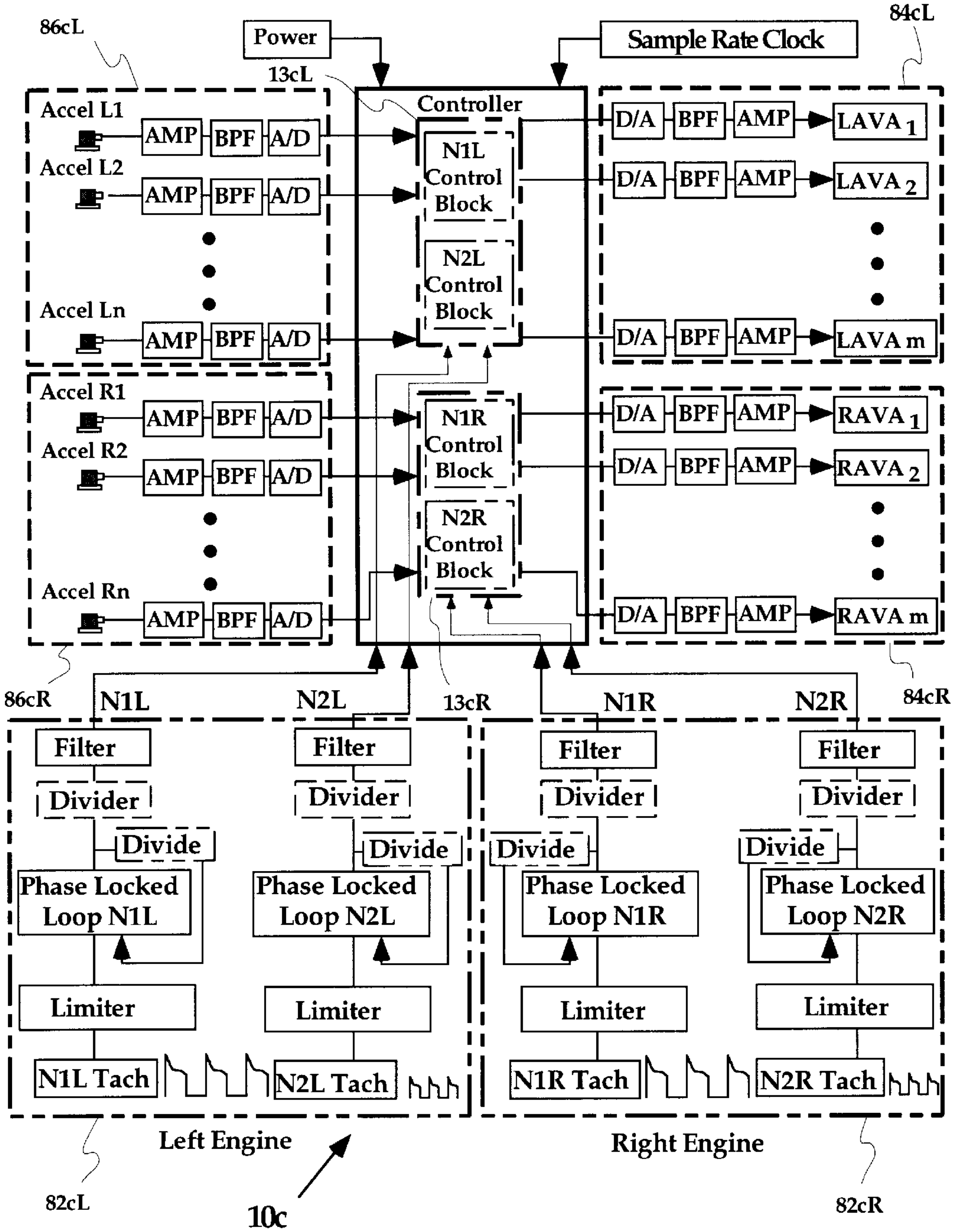
FIG. 6*c* is a schematic block diagram of the third embodiment of the present invention ASC system described with reference to FIG. 4*b,*

FIG. 6c illustrates a block diagram of the ASC system 10c previously described with reference to FIG. 4b. In this embodiment, the ASC system 10c is further decoupled in that the right adaptive control 13cR only receives error information from the right error bank 86cR (including n number of accelerometers accel L1 through accel Ln) and the left adaptive control 13cL only receives error information from the left error bank 86cL (including n number of right accelerometers accel R1 through accel Rn). Likewise, the left engine reference signal generating means 82cL is provided only to be used in the left adaptive control 13cL for driving the left AVA bank 84cL (including m number of left AVAs $LAVA_1$ through $LAVA_m$) and right engine reference signal generating means 82cR is provided only to be used in the right adaptive control 13cR for driving the right AVA bank 84aR (including m number of right AVAs $RAVA_1$ through $RAVA_m$). Generally, it is preferable that number of left accelerometers exceed the number of left AVAs (n>m) and number of right accelerometers exceed the number of right AVAs (n>m).

FIG. 7a illustrates an ANVC system 10k, and in particular, is intended to aid in describing alternative reference signal processing that may be employed, which has potentially broader applicability than the ASC systems previously described with reference to the previous FIG. 3*a* through FIG. 6*c*. In particular, this aspect of the invention relates to a novel means and method for providing an input signal to an adaptive control 13*k*. In more detail, the ANVC system 10*k* (including the subset ASC system, example 10*a* (FIG. 3*a*) embodying the invention comprises at least one reference sensor 50*k*, which can be either a tachometer sensor or an accelerometer for providing a signal indicative of a disturbance source 18*k*, such as an aircraft engine, automobile engine, or the like. The raw signal indicative of, for example, N1R of the vehicle engine (generally a sinusoid-like wave) is conditioned within input conditioning block 89*k* to provide a conditioned reference signal. Within input conditioning block is a limiter 55*k* which conditions the signal as is shown with reference to FIG. 7*b*, a PLL 57*k*, and a Divider 58*k*.

First, the sinusoid wave 90*k* indicative of N1R is transformed into a square wave via a hysteresis process step. The square wave 91*k* indicative of the N1R frequency is generated by triggering on predetermined positive (+) voltage and negative (−) voltage values of the sinusoid wave 90*k*. The peak values of the square wave 91*k* correspond to the peak values of the sinusoid wave 90*k*. Next, as shown in FIG. 7*c*, the magnitude of the square wave signal 91*k* is clipped within limiter 55*k* to predetermined voltage values (+V, −V) to form the clipped signal 92*k* indicative of the N1R frequency. This clipped signal 92*k* is then inputted into a PLL 57*k*. The PLL 57*k* locks onto the predominant N1R frequency component. A divider 93*k* in the comparator leg 94*k* divides by an integer multiple, with the resultant effect of multiplying up the frequency of the clipped signal 92*k* by that integer multiple. If a tachometer sensor is used for the reference sensor 50*k*, the integer multiple may comprise a gear ratio portion, as before described, and also some preferably power-of-two factor (e.g. 8, 16, 32, 64, 128, 256, . . . ) for further multiplying up the signal frequency. Optional divide 58*k* is needed only if the raw tachometer signal indicative of N1R needs to be further geared up or down. If a reference accelerometer is used, the signal will already be at the N1R frequency and divider 58*k* would be unneeded. Additional conditioning, such as using ALEs, may be required before entering the conditioning block 89*k* if the raw N1R signal has unacceptable superimposed noise thereon.

The conditioned and multiplied reference signal 95*k* exiting the conditioning block 89*k* is provided to digital input generator 99*k* which includes a counter, such as a modulo counter 96*k*. The modulo counter 96*k* continuously generates a count from a minimum value to a maximum value. For example, the count may be from 0 to a power-of-two number minus one (example, $2^R-1=7$, 15, 31, 63, 127, 255, where R=the number of bits), as shown in FIG. 7*d*. The count is based upon the conditioned reference signal. In other words, for each cycle, example cycle 1, cycle 2, . . . , the signal is divided into a power-of-two number of increments (counts). When the counter gets to the end, it simply starts over at zero. A storage means, such as a lookup table 97*k*, has sinusoidal input values stored therein representative of each count. The individual input values stored in the table for each count, as shown in FIG. 7*e*, are determined according to the equation:

$$\text{Value}=\text{Sin}\,[\text{count}\times(2\,\pi/\text{total count})]$$

For example, if the frequency multiplier were 256, then there would be 256 counts per cycle and 256 values (0 through 255) stored in the table. Means for extracting the individual ones of the stored input values, such as a digital Input/Output (IO) 98*k* which reads the count from modulo counter 96*k* and provides the count to software which then extracts the appropriate corresponding input value from the lookup table 97*k*. The stream of input values extracted from the table 97*k* which is based upon the count from modulo counter 96*k* collectively comprise an input signal indicative of N1R which can be fed directly to the adaptive control filter 11*k* (example an FIR filter) in adaptive control process 13*k*.

The signal optionally may be fed to an error path model 72*k* to be used by the adaptive update means 71*k* along with the error sensor information from at least one error sensor, for example, a microphone 42*k*, or an accelerometer 63*k* to update the weights of the control filter 11*k*. The update method is preferably Filtered-x LMS, or the like. The output of the control 13*k* is used to drive at least one output transducer, for example, an active mount 12*k*, a loudspeaker 16*k*, or an AVA 40*k* to produce active noise and/or vibration and control noise and/or vibration within control volume 44*k*. It should be understood that the use of the modulo counter is optional and that an signal indicative of N1 could be used directly by the adaptive control. It should also be understood that multiple modulo counters could be used to provide multiplied signals indicative of N1R, N2R, N1L, N2L for vehicles such as aircraft. Further, if a quadrature-type control is utilized, it should be understood that a second signal could be derived which lags by 90° from the first signal by implementing a delay of ¼ wavelength (¼ the total number of counts). Therefore, a sine and a cosine wave for input to the adaptive control could be generated from the table. Similarly, a separate table could include the phase shifted (cosine) values.

While several embodiments, including the preferred embodiment of the present invention, have been described in detail, various modifications, alterations, changes and adaptations to the aforementioned may be made without departing from the spirit and scope of the present invention defined in the appended claims. It is intended that all such modifications, alterations and changes be considered part of the present invention.

What is claimed is:

1. An Active Structural Control (ASC) system for controlling acoustic noise and/or vibration generated within an aircraft cabin that results from vibration generated by at least one engine attached to a pylon structure by mounts, said vibration being transmitted into said pylon structure which attaches between said at least one engine and an aircraft fuselage, said pylon structure preferably including a yoke and a spar, and causes vibration of said aircraft fuselage, thereby generating said acoustic noise and/or vibration within said aircraft cabin, said ASC system comprising:

(a) a plurality of error sensors for providing a plurality of error signals, (b) at least one reference sensor associated with said at least one engine for providing at least one reference signal selected from a group consisting of:

(i) a first reference signal indicative of an N1 engine rotation, and (ii) a second reference signal indicative of an N2 engine rotation, (c) a plurality of Active Vibration Absorbers (AVAs) attached to said yoke at positions other than through said mounts, wherein said plurality of active vibration absorbers are further comprised of:

a Single Degree Of Freedom (SDOF) AVA located at at least one of a first and a second terminal end portion of said yoke and which is tuned to exhibit a resonant frequency which substantially coincides with an N2 engine rotation frequency and which acts in a substantially radial direction, and at least four Single Degree Of Freedom (SDOF) AVAs located on said yoke at a base portion thereof where said yoke connects to said spar wherein at least one of said at least four SDOF AVAs is tuned such that it exhibits a natural frequency which substantially coincides with an N1 engine rotation frequency; and (d) a controller for processing said at least one selected from said group consisting of said first reference signal and said second reference signal and said plurality of error signals and providing a plurality of output signals to said plurality of AVAs to effectuate vibration of said yoke and resultantly control acoustic noise within said aircraft cabin.

2. A method of actively controlling acoustic noise and/or vibration generated within an aircraft cabin wherein said acoustic noise and/or vibration is generated by vibration transmitted through an intermediate pylon structure attached to an engine by mounts, said pylon structure including a spar and a yoke and in which said pylon structure is connected intermediate between an aircraft engine and an aircraft fuselage, said method comprising the steps of:

(a) generating a plurality of error signals by a plurality of error sensors, (b) generating at least one signal indicative selected from a group consisting of:

(i) a signal indicative of an N1 engine rotation of said aircraft engine, and (ii) a signal indicative of an N2 engine rotation of said aircraft engine, (c) providing said plurality of error signals and said at least one reference signal to a controller, (d) processing said at least one reference signal and said error signals within an adaptive control operating within said controller, updating of said adaptive control taking place according to an adaptive control algorithm to provide a plurality of output signals corresponding to said at least one reference signal, (e) driving a plurality of Active Vibration Absorbers (AVAs) attached to said pylon structure at positions other than at said mounts, according to said plurality of output signals at at least one frequency selected from a group consisting of:

(i) an N1 engine rotational frequency, and (ii) an N2 engine rotational frequency, wherein a resultant effect is to control said acoustic noise within said aircraft cabin; and wherein said plurality of AVAs are further comprised of at least one Single Degree Of Freedom (SDOF) AVA located at a terminal end portion of said yoke wherein said at least one Single Degree Of Freedom (SDOF) AVA is tuned to exhibit a natural frequency which substantially coincides with an N2 engine rotation frequency and at least one Single Degree Of Freedom (SDOF) AVA located on said yoke at a base portion thereof where said yoke connects to said spar wherein said at least one SDOF AVA located on said yoke at said base portion is tuned to exhibit a natural frequency which substantially coincides with an N1 engine rotation frequency.

3. A method of actively controlling acoustic noise and/or vibration generated within an aircraft cabin wherein said acoustic noise and/or vibration is generated by vibration transmitted through an intermediate pylon structure attached to an engine by mounts, said pylon structure including a spar and a yoke and in which said pylon structure is connected intermediate between an aircraft engine and an aircraft fuselage, said method comprising the steps of:

(a) generating a plurality of error signals by a plurality of error sensors, (b) generating at least one signal indicative selected from a group consisting of:

(i) a signal indicative of an N1 engine rotation of said aircraft engine, and (ii) a signal indicative of an N2 engine rotation of said aircraft engine, (c) providing said plurality of error signals and said at least one reference signal to a controller, (d) processing said at least one reference signal and said error signals within an adaptive control operating within said controller, updating of said adaptive control taking place according to an adaptive control algorithm to provide a plurality of output signals corresponding to said at least one reference signal, (e) driving a plurality of Active Vibration Absorbers (AVAs) attached to said pylon structure at positions other than at said mounts, according to said plurality of output signals at at least one frequency selected from a group consisting of:

(i) an N1 engine rotational frequency, and (ii) an N2 engine rotational frequency, wherein a resultant effect is to control said acoustic noise within said aircraft cabin; and wherein the plurality of AVAs includes at least one Single Degree Of Freedom (SDOF) AVA directed to act substantially in one direction selected from a group consisting of a radial direction, a tangential direction, and a fore and aft direction wherein said at least one SDOF AVA is located on said yoke at a base portion thereof where said yoke connects to said spar.

4. A method of actively controlling acoustic noise and/or vibration generated within an aircraft cabin wherein said acoustic noise and/or vibration is generated by vibration transmitted through an intermediate pylon structure attached to an engine by mounts, said pylon structure including a spar and a yoke and in which said pylon structure is connected intermediate between an aircraft engine and an aircraft fuselage, said method comprising the steps of:

(a) generating a plurality of error signals by a plurality of error sensors, (b) generating at least one signal indicative selected from a group consisting of:

(i) a signal indicative of an N1 engine rotation of said aircraft engine, and (ii) a signal indicative of an N2 engine rotation of said aircraft engine, (c) providing said plurality of error signals and said at least one reference signal to a controller, (d) processing said at least one reference signal and said error signals within an adaptive control operating within said controller, updating of said adaptive control taking place according to an adaptive control algorithm to provide a plurality of output signals corresponding to said at least one reference signal, (e) driving a plurality of Active Vibration Absorbers (AVAs) attached to said pylon structure at positions other than at said mounts, according to said plurality of output signals at at least one frequency selected from a group consisting of:

(i) an N1 engine rotational frequency, and (ii) an N2 engine rotational frequency, wherein a resultant effect is to control said acoustic noise within said aircraft cabin; and wherein said plurality of active vibration absorbers are further comprised of:

a Single Degree Of Freedom (SDOF) AVA located at at least one of a first and a second terminal end portion of said yoke and which is tuned to exhibit a resonant frequency which substantially coincides with an N2 engine rotation frequency and which acts in a substantially radial direction, and at least four Single Degree Of Freedom (SDOF) AVAs located on said yoke at a base portion thereof where said yoke connects to said spar wherein at least one of said at least four SDOF AVAs is tuned such that it exhibits a natural frequency which substantially coincides with an N1 engine rotation frequency.

5. An Active Structural Control (ASC) system for controlling acoustic noise and/or vibration generated within an aircraft cabin that results from vibration generated by at least one engine, said vibration which is transmitted into a pylon structure which attaches between said at least one engine and an aircraft fuselage, said pylon structure preferably including a yoke and a spar, and causes vibration of said aircraft fuselage, thereby generating said acoustic noise and/or vibration within said aircraft cabin, said ASC system comprising:

(a) a plurality of error sensors for providing a plurality of error signals, (b) at least one reference sensor associated with said at least one engine for providing at least one reference signal selected from a group consisting of:

(i) a first reference signal indicative of an N1 engine rotation, and (ii) a second reference signal indicative of an N2 engine rotation, (c) a plurality of Active Vibration Absorbers (AVAs) directly attached by brackets to said yoke, said plurality of AVAs including at least one Single Degree Of Freedom (SDOF) AVA located at a terminal end portion of said yoke which is tuned to exhibit a natural frequency which substantially coincides with an N2 engine rotation frequency and at least one Single Degree Of Freedom (SDOF) AVA located on said yoke at a base portion thereof where said yoke connects to said spar wherein said at least one SDOF AVA located on said yoke at said base portion is tuned to exhibit a natural frequency which substantially coincides with an N1 engine rotation frequency, and (d) a controller for processing said at least one selected from said group consisting of said first reference signal and said second reference signal and said plurality of error signals and providing a plurality of output signals to said plurality of AVAs to effectuate vibration of said yoke and resultantly control acoustic noise and vibration within said aircraft cabin.

6. An Active Structural Control (ASC) system for controlling acoustic noise and/or vibration generated within an aircraft cabin that results from vibration generated by at least one engine, said vibration which is transmitted into a pylon structure which attaches between said at least one engine and an aircraft fuselage, said pylon structure preferably including a yoke and a spar, and causes vibration of said aircraft fuselage, thereby generating said acoustic noise and/or vibration within said aircraft cabin, said ASC system comprising:

(a) a plurality of error sensors for providing a plurality of error signals, (b) at least one reference sensor associated with said at least one engine for providing at least one reference signal selected from a group consisting of:

(i) a first reference signal indicative of an N1 engine rotation, and (ii) a second reference signal indicative of an N2 engine rotation, (c) a plurality of Active Vibration Absorbers (AVAs) directly attached by brackets to said yoke, said plurality of AVAs directed to produce active forces in at least two directions selected from the group consisting of radial, tangential, and fore and aft directions, and (d) a controller for processing said at least one selected from said group consisting of said first reference signal and said second reference signal and said plurality of error signals and providing a plurality of output signals to said plurality of AVAs to effectuate vibration of said yoke and resultantly control acoustic noise and vibration within said aircraft cabin.

7. An Active Structural Control (ASC) system for controlling acoustic noise and/or vibration generated within an aircraft cabin that results from vibration generated by at least one engine, said vibration which is transmitted into a pylon structure which attaches between said at least one engine and an aircraft fuselage, said pylon structure preferably including a yoke and a spar, and causes vibration of said aircraft fuselage, thereby generating said acoustic noise and/or vibration within said aircraft cabin, said ASC system comprising:

(a) a plurality of error sensors for providing a plurality of error signals, (b) at least one reference sensor associated with said at least one engine for providing at least one reference signal selected from a group consisting of:

(i) a first reference signal indicative of an N1 engine rotation, and (ii) a second reference signal indicative of an N2 engine rotation, (c) a plurality of Active Vibration Absorbers (AVAs) directly attached by brackets to said yoke, said plurality of AVAs are further comprised of AVAs substantially directed to produce active forces in at least two directions selected from the group consisting of radial, tangential, and fore and aft directions, said plurality of AVAs including AVAs selected from group consisting of Single Degree Of Freedom (SDOF) AVAs and Multiple Degree Of Freedom (MDOF) AVAs, and (d) a controller for processing said at least one selected from said group consisting of said first reference signal and said second reference signal and said plurality of error signals and providing a plurality of output signals to said plurality of AVAs to effectuate vibration of said yoke and resultantly control acoustic noise and vibration within said aircraft cabin.

8. An Active Structural Control (ASC) system for controlling acoustic noise and/or vibration generated within an aircraft cabin that results from vibration generated by at least one engine, said vibration which is transmitted into a pylon structure which attaches between said at least one engine and an aircraft fuselage, said pylon structure preferably including a yoke and a spar, and causes vibration of said aircraft fuselage, thereby generating said acoustic noise and/or vibration within said aircraft cabin, said ASC system comprising:

(a) a plurality of error sensors for providing a plurality of error signals, (b) at least one reference sensor associated with said at least one engine for providing at least one reference signal selected from a group consisting of:

(i) a first reference signal indicative of an N1 engine rotation, and (ii) a second reference signal indicative of an N2 engine rotation, (c) a plurality of Active Vibration Absorbers (AVAs) directly attached by brackets to said yoke, said plurality of AVAs including at least one Single Degree Of Freedom (SDOF) AVA directed to act substantially in one direction selected from a group consisting of a radial direction, a tangential direction, and a fore and aft direction wherein said at least one SDOF AVA is located on said yoke at a base portion thereof where said yoke connects to said spar, and (d) a controller for processing said at least one selected from said group consisting of said first reference signal and said second reference signal and said plurality of error signals and providing a plurality of output signals to said plurality of AVAs to effectuate vibration of said yoke and resultantly control acoustic noise and vibration within said aircraft cabin.

9. An Active Structural Control (ASC) system for controlling acoustic noise and/or vibration generated within an aircraft cabin that results from vibration generated by at least one engine, said vibration which is transmitted into a pylon structure which attaches between said at least one engine and an aircraft fuselage, said pylon structure preferably including a yoke and a spar, and causes vibration of said aircraft fuselage, thereby generating said acoustic noise and/or vibration within said aircraft cabin, said ASC system comprising:

(a) a plurality of error sensors for providing a plurality of error signals, (b) at least one reference sensor associated with said at least one engine for providing at least one reference signal selected from a group consisting of:

(i) a first reference signal indicative of an N1 engine rotation, and (ii) a second reference signal indicative of an N2 engine rotation, (c) a plurality of Active Vibration Absorbers (AVAs) directly attached by brackets to said yoke, said plurality of Active Vibration Absorbers (AVAs) including a first bank of plurality of AVAs and a second bank of plurality of AVAs each said bank including a plurality of Single Degree Of Freedom (SDOF) AVAs wherein at least one of said plurality of SDOF AVAs within each said bank acts in a substantially radial direction and at least one of said plurality of SDOF AVAs within each said bank acts in a substantially tangential direction, and (d) a controller for processing said at least one selected from said group consisting of said first reference signal and said second reference signal and said plurality of error signals and providing a plurality of output signals to said plurality of AVAs to effectuate vibration of said yoke and resultantly control acoustic noise and vibration within said aircraft cabin wherein said controller is decoupled to have a first multiple of control filters and a second multiple of control filters, said first multiple is used to control a first bank of plurality of AVAs associated with a first aircraft engine, and said second multiple is used to control a second bank of plurality of AVAs associated with a second aircraft engine.

10. An Active Structural Control (ASC) system for controlling acoustic noise and/or vibration generated within an aircraft cabin that results from vibration generated by at least one engine, said vibration which is transmitted into a pylon structure which attaches between said at least one engine and an aircraft fuselage, said pylon structure preferably including a yoke and a spar, and causes vibration of said aircraft fuselage, thereby generating said acoustic noise and/or vibration within said aircraft cabin, said ASC system comprising:

(a) a plurality of error sensors for providing a plurality of error signals, (b) at least one reference sensor associated with said at least one engine for providing at least one reference signal selected from a group consisting of:

(i) a first reference signal indicative of an N1 engine rotation, and (ii) a second reference signal indicative of an N2 engine rotation, (c) a plurality of Active Vibration Absorbers (AVAs) directly attached by brackets to said yoke, said plurality of AVAs further comprising at least one Single Degree Of Freedom (SDOF) AVA, and at least one Multiple Degree Of Freedom (MDOF) AVA, and (d) a controller for processing said at least one selected from said group consisting of said first reference signal and said second reference signal and said plurality of error signals and providing a plurality of output signals to said plurality of AVAs to effectuate vibration of said yoke and resultantly control acoustic noise and vibration within said aircraft cabin.

11. An Active Structural Control (ASC) system for controlling acoustic noise and/or vibration generated within an aircraft cabin that results from vibration generated by at least one engine, said vibration which is transmitted into a pylon structure which attaches between said at least one engine and an aircraft fuselage, said pylon structure preferably including a yoke and a spar, and causes vibration of said aircraft fuselage, thereby generating said acoustic noise and/or vibration within said aircraft cabin, said ASC system comprising:

(a) a plurality of error sensors for providing a plurality of error signals, (b) at least one reference sensor associated with said at least one engine for providing at least one reference signal selected from a group consisting of:

(i) a first reference signal indicative of an N1 engine rotation, and (ii) a second reference signal indicative of an N2 engine rotation, (c) a plurality of Active Vibration Absorbers (AVAs) directly attached by brackets to said yoke, said plurality of AVAs further comprising an AVA set including orthogonally arranged AVAs, and (d) a controller for processing said at least one selected from said group consisting of said first reference signal and said second reference signal and said plurality of error signals and providing a plurality of output signals to said plurality of AVAs to effectuate vibration of said yoke and resultantly control acoustic noise and vibration within said aircraft cabin.

12. An Active Structural Control (ASC) system for controlling acoustic noise and/or vibration generated within an aircraft cabin that results from vibration generated by at least one engine attached by mounts to a pylon structure, said vibration being transmitted into the pylon structure which attaches between said at least one engine and an aircraft fuselage, said pylon structure preferably including a yoke and a spar, and causes vibration of said aircraft fuselage, thereby generating said acoustic noise and/or vibration within said aircraft cabin, said ASC system comprising:

(a) a plurality of error sensors for providing a plurality of error signals, (b) at least one reference sensor associated with said at least one engine for providing at least one reference signal indicative of an engine rotation, (c) a plurality of Active Vibration Absorbers (AVAs) attached to said yoke other then through said mounts, said plurality of AVAs including a plurality of orthoginally-oriented Multiple Degree Of Freedom (MDOF) AVAs located on said yoke at a base portion thereof where said yoke connects to said spar, and (d) a controller for processing said at least one selected from said group consisting of said first reference signal and said second reference signal and said plurality of error signals and providing a plurality of output signals to said plurality of AVAs to effectuate vibration of said yoke and resultantly control acoustic noise and vibration within said aircraft cabin.

* * * * *